(12) United States Patent
Small et al.

(10) Patent No.: US 6,316,270 B1
(45) Date of Patent: Nov. 13, 2001

(54) ACID BASE OR GENERATOR

(75) Inventors: Hamish Small, Leland, MI (US); Nebojsa Avdalovic, San Jose; Yan Liu, Santa Clara, both of CA (US)

(73) Assignee: Dionex Corporation, Sunnyvale, CA (US)

(*) Notice: Subject to any disclaimer, the term of this patent is extended or adjusted under 35 U.S.C. 154(b) by 0 days.

(21) Appl. No.: 09/470,192

(22) Filed: Dec. 23, 1999

Related U.S. Application Data

(60) Division of application No. 09/006,096, filed on Jan. 13, 1998, now Pat. No. 6,036,921, which is a continuation-in-part of application No. 08/783,317, filed on Jan. 15, 1997, now abandoned.

(51) Int. Cl.[7] .......................... G01N 30/02; G01N 30/26
(52) U.S. Cl. .................. 436/161; 436/150; 73/61.53; 73/61.56; 204/551; 204/647; 205/335; 210/656; 210/662; 210/670
(58) Field of Search ............................ 436/161, 150; 422/70, 82.02; 73/61.53, 61.56; 204/551, 647; 205/335; 210/198.2, 263, 269, 656, 662, 670

(56) References Cited

U.S. PATENT DOCUMENTS

| | | |
|---|---|---|
| 2,396,934 | 3/1946 | Wallace .................................. 210/28 |
| 3,897,213 | 7/1975 | Stevens et al. . |
| 3,920,397 | 11/1975 | Small et al. . |
| 3,925,019 | 12/1975 | Small et al. . |
| 3,926,559 | 12/1975 | Stevens . |
| 5,045,204 | 9/1991 | Dasgupta et al. ..................... 210/635 |
| 5,423,965 | 6/1995 | Kunz ................................. 204/182.4 |
| 5,759,405 | 6/1998 | Anderson, Jr. et al. ............. 210/656 |
| 5,914,025 | 6/1999 | Small ................................... 205/789 |
| 6,036,921 | * 3/2000 | Small et al. . |

FOREIGN PATENT DOCUMENTS 0 180 321    5/1986   (EP) .

* cited by examiner

*Primary Examiner*—Jan Ludlow
(74) *Attorney, Agent, or Firm*—Flehr Hohbach Test Albritton & Herbert LLP; David J. Brezner

(57) ABSTRACT

A method for generating high purity acid or base in an aqueous stream for use as an eluent for chromatography and, particularly, ion chromatography. For generating a base for anion chromatography, the aqueous stream is directed through a cation exchange bed having a first strongly acidic and a second weakly acidic portions. An electrical potential is applied to the bed. Cations on the bed electromigrate into the aqueous stream while hydroxide ions are electrolytically generated to form a base-containing eluent. Anions to be detected and the generated eluent flow through a chromatographic separator. The chromatographic effluent flows past a detector.

26 Claims, 16 Drawing Sheets

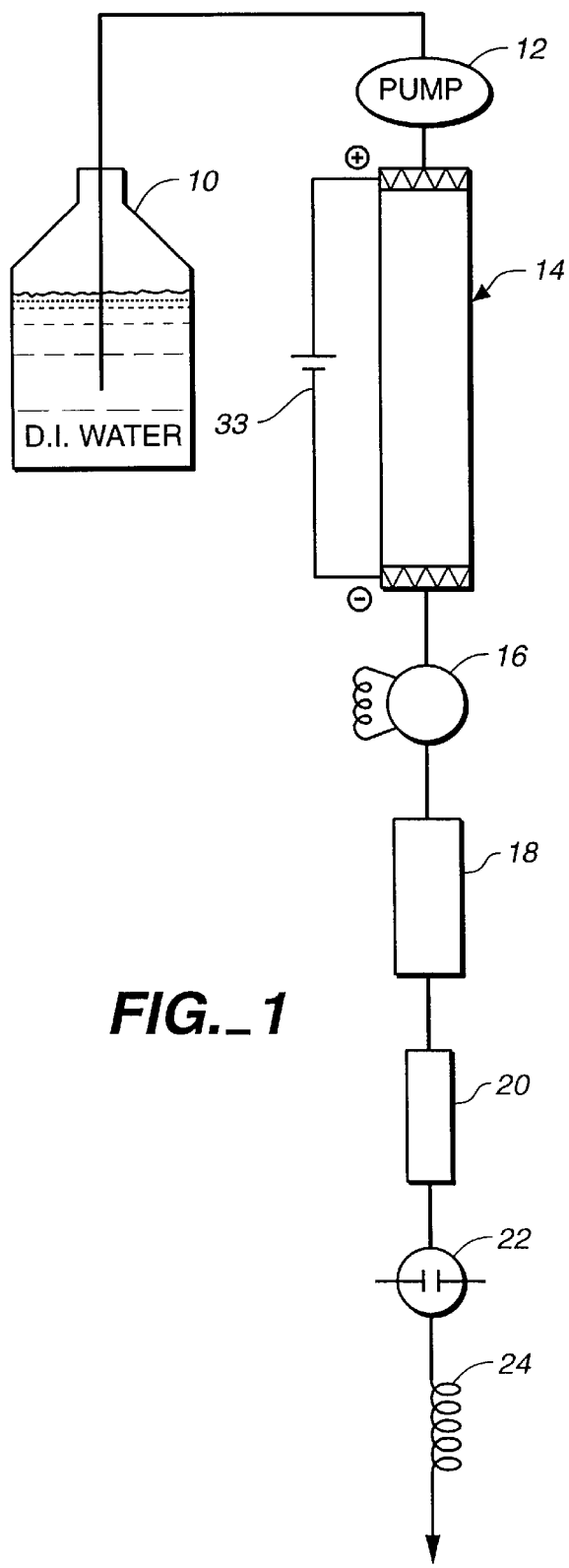
FIG._1
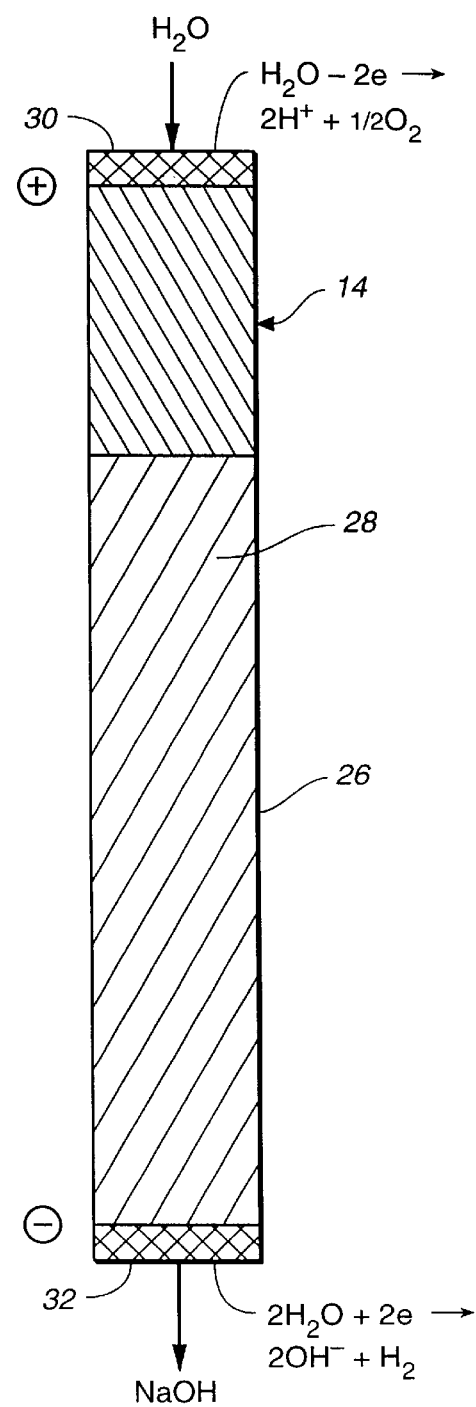
FIG._2

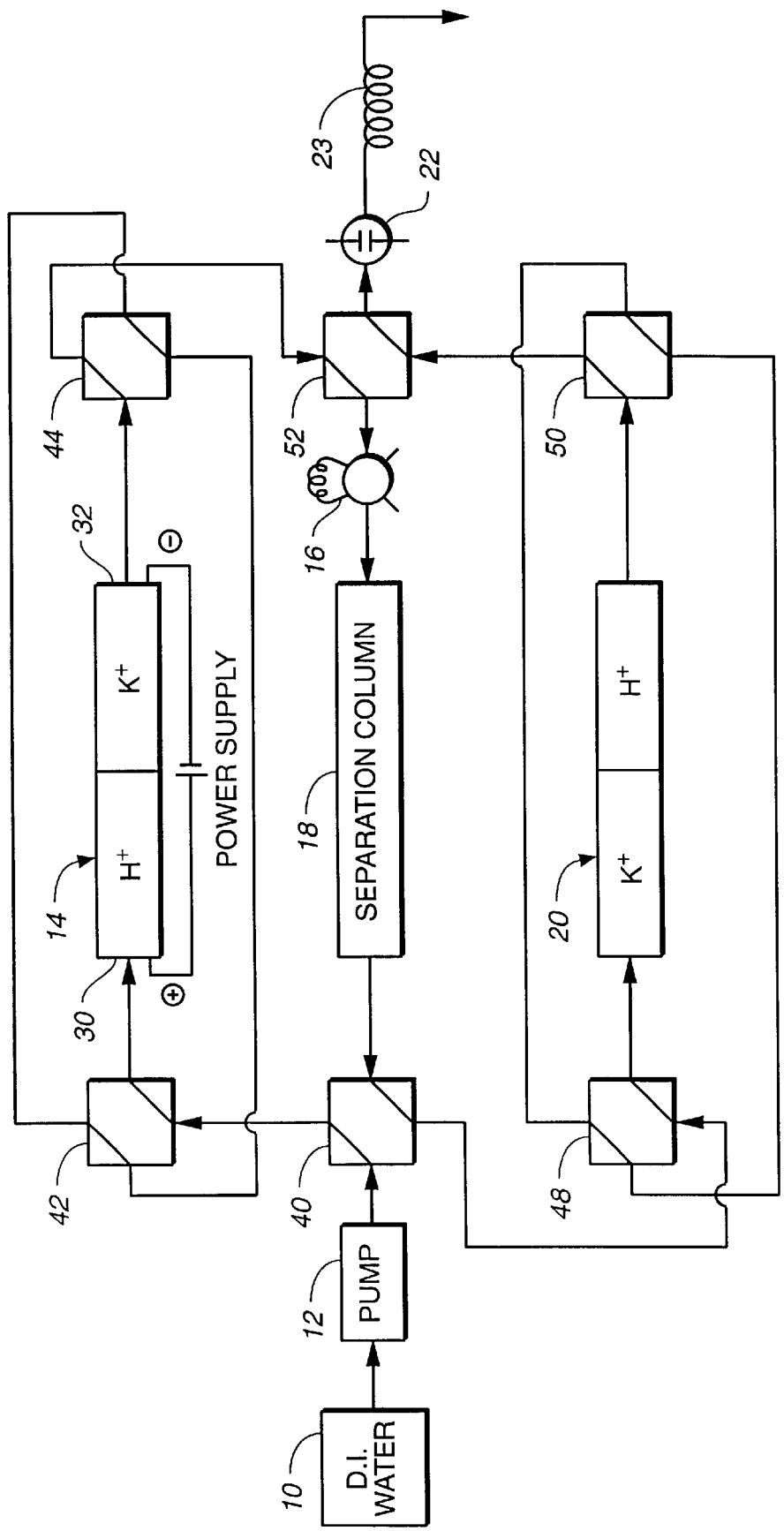
FIG._3

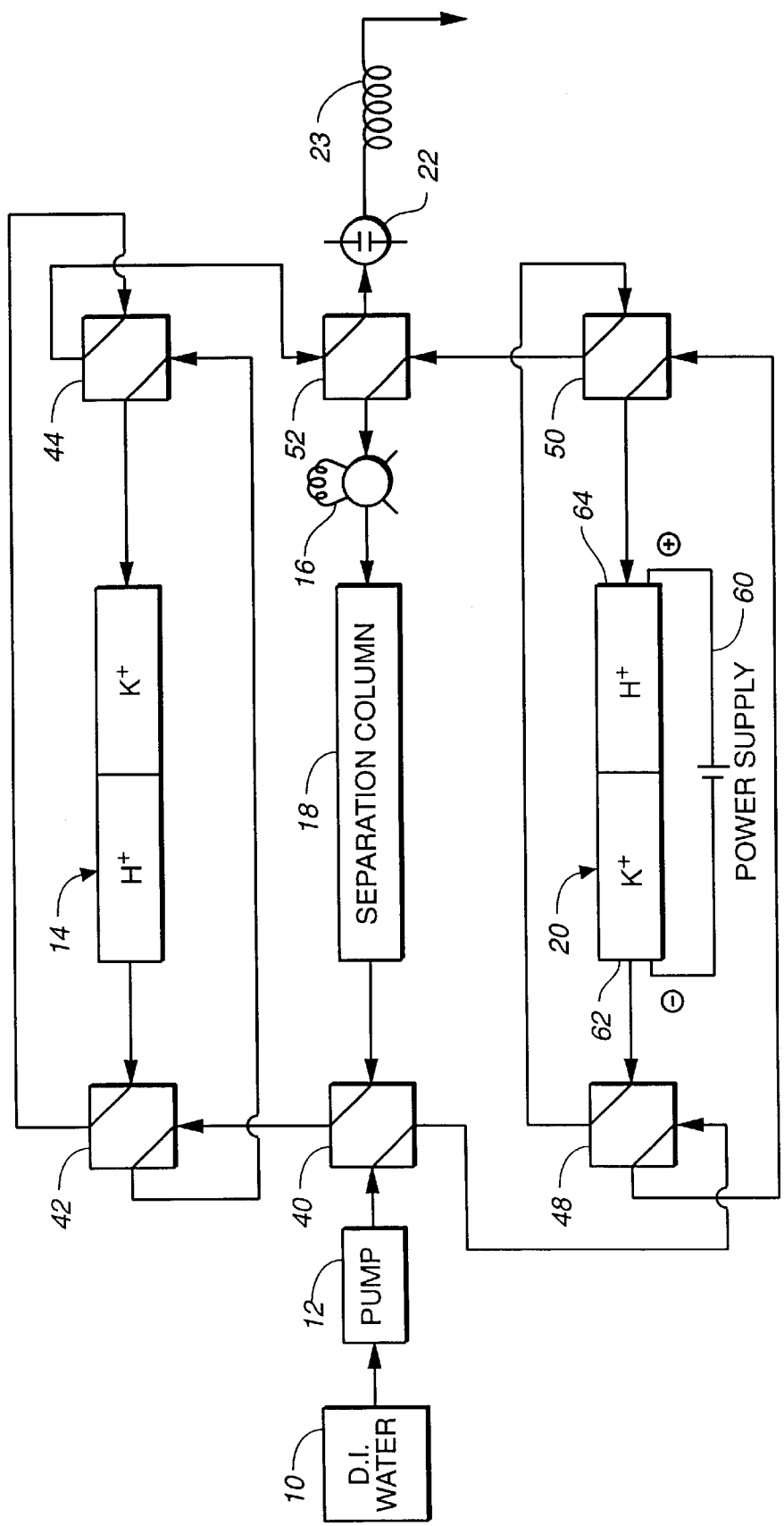
FIG._4

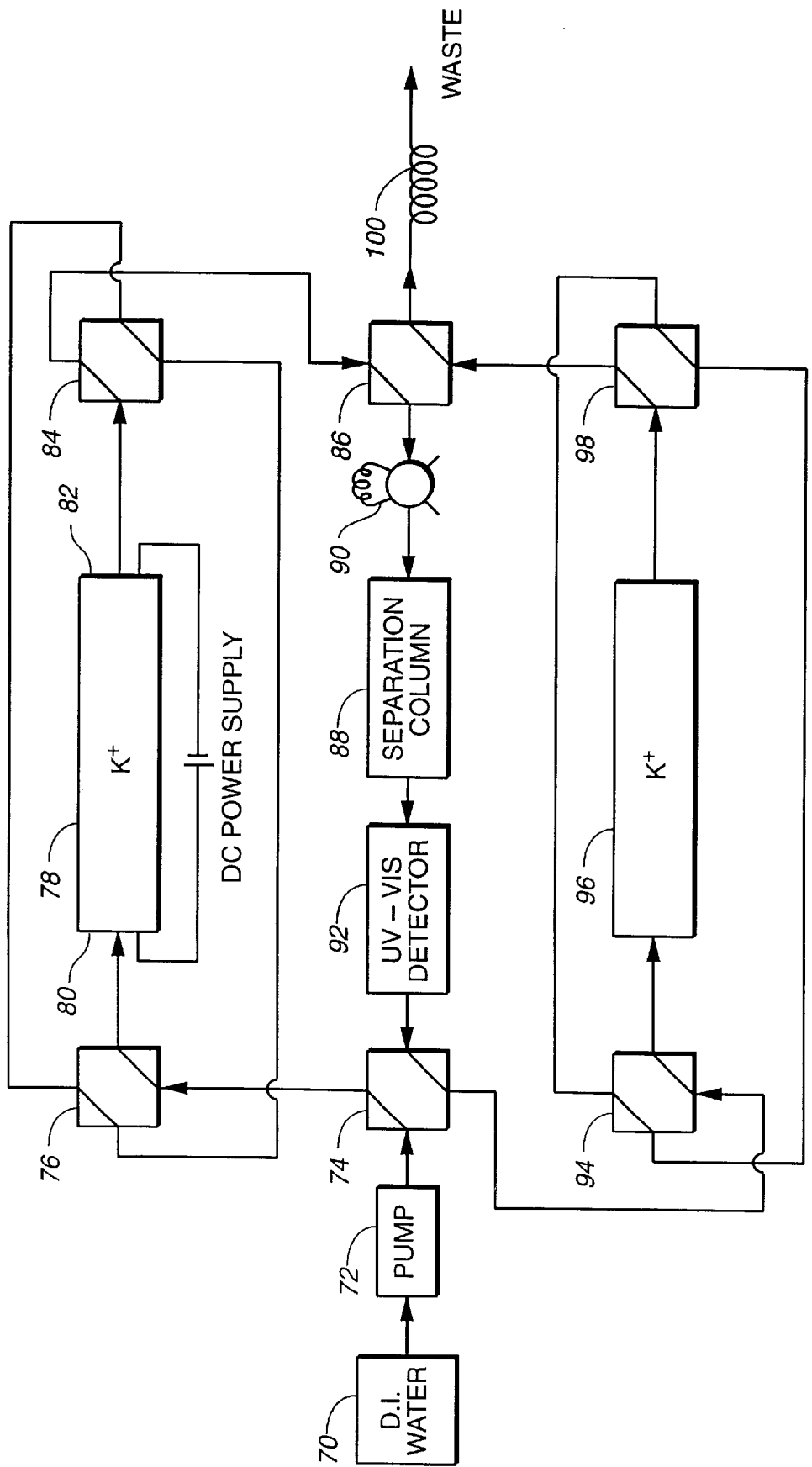
FIG._5

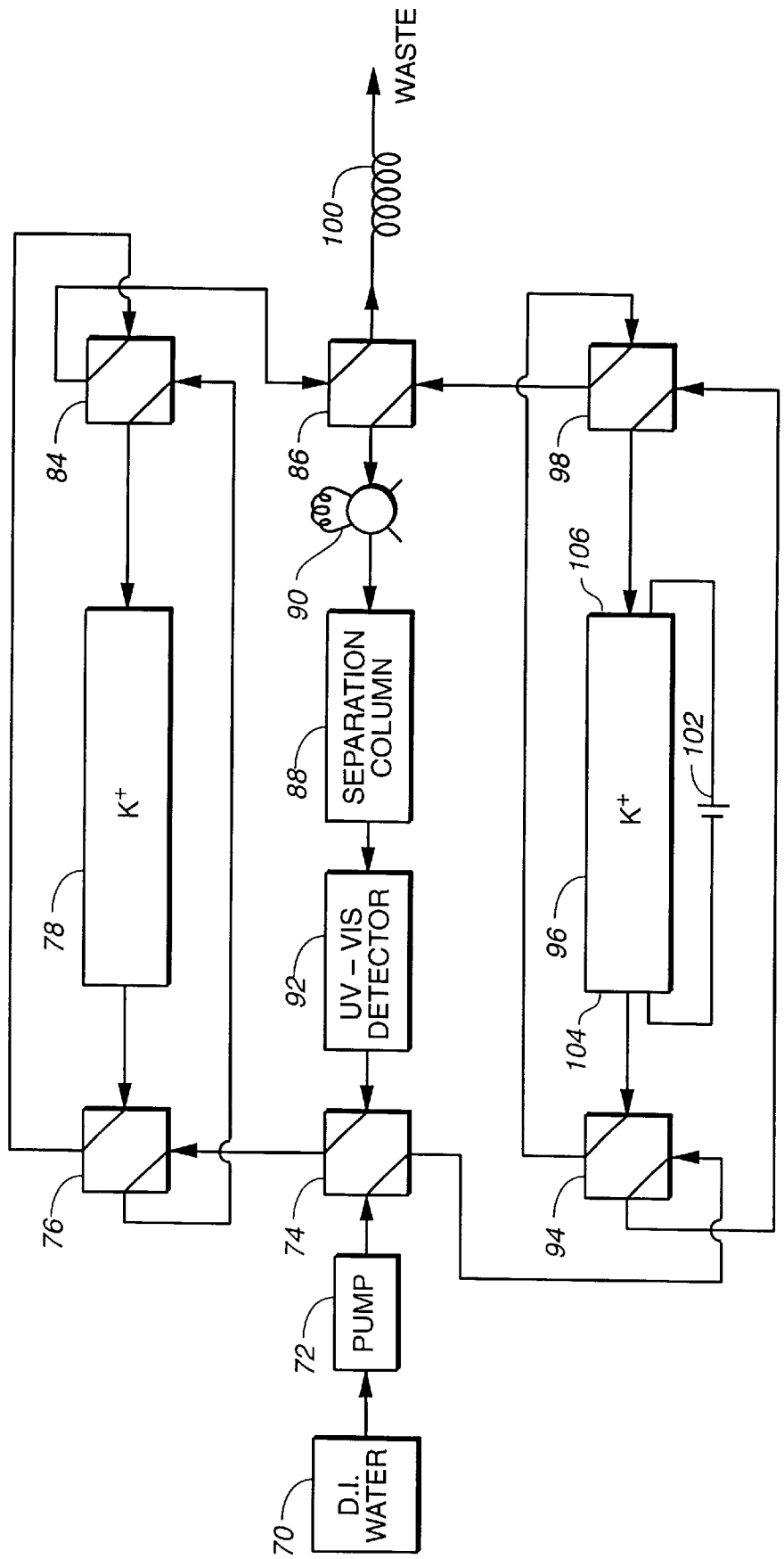
FIG._6

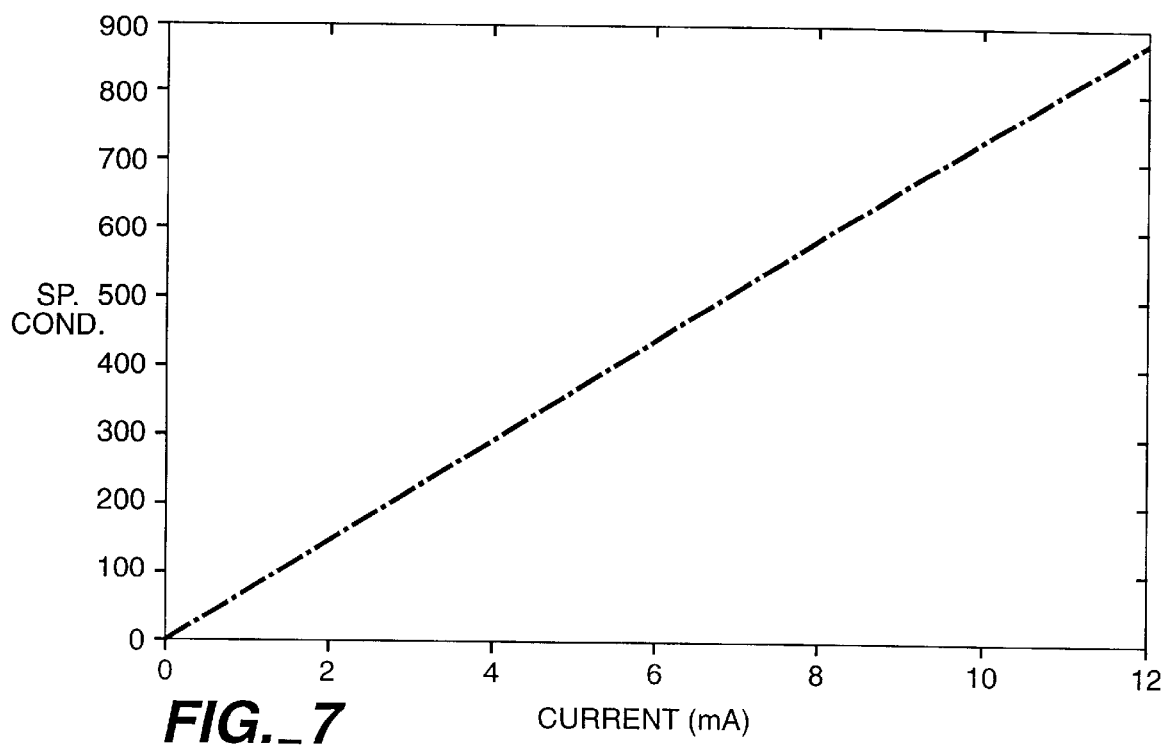
FIG._7
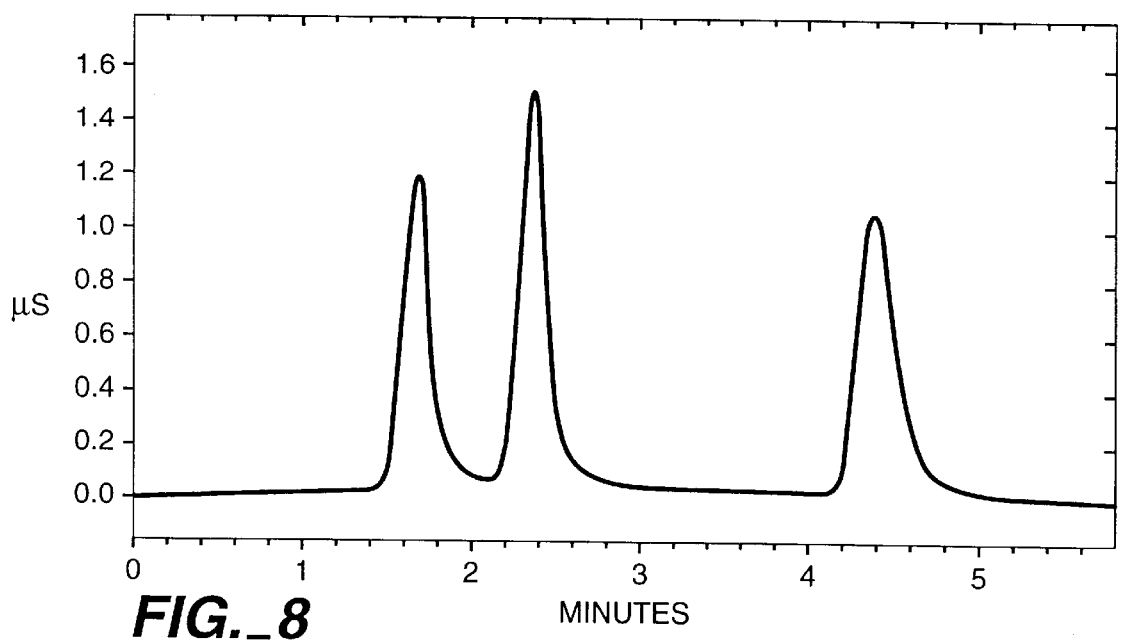
FIG._8

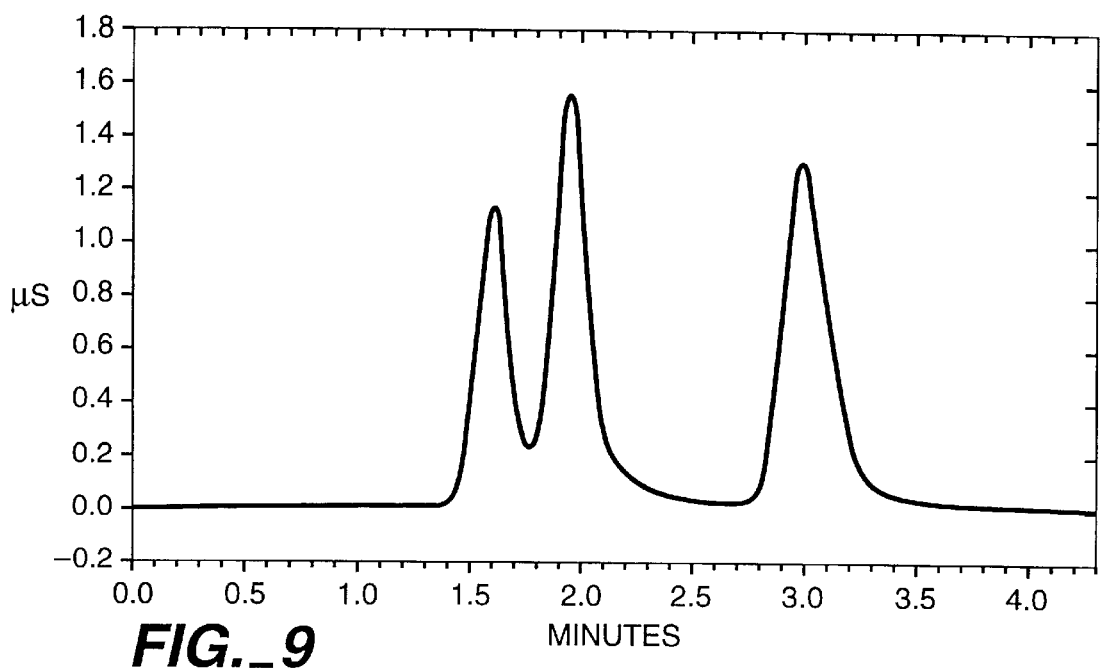
FIG._9
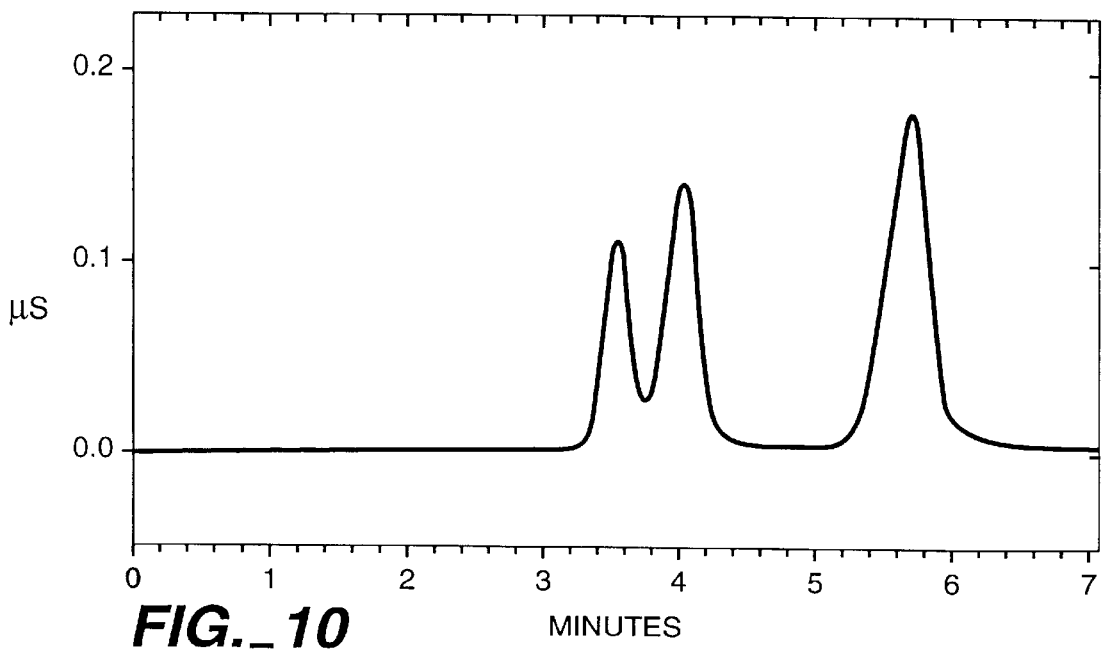
FIG._10

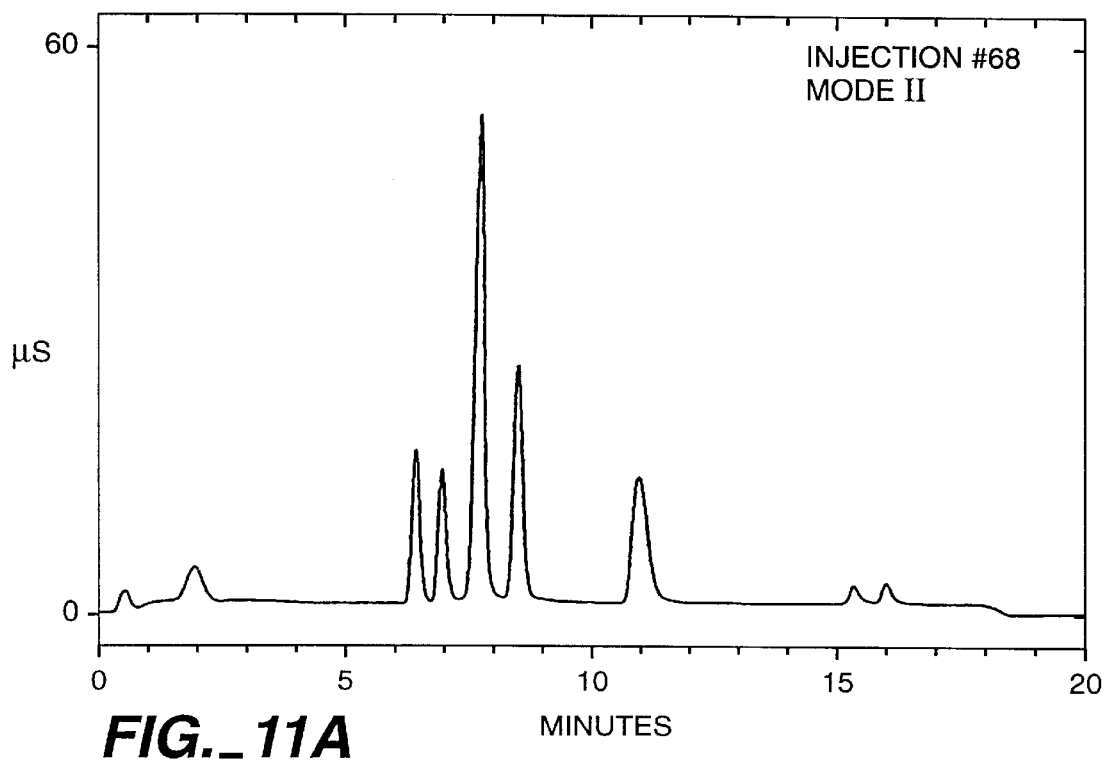
FIG._11A
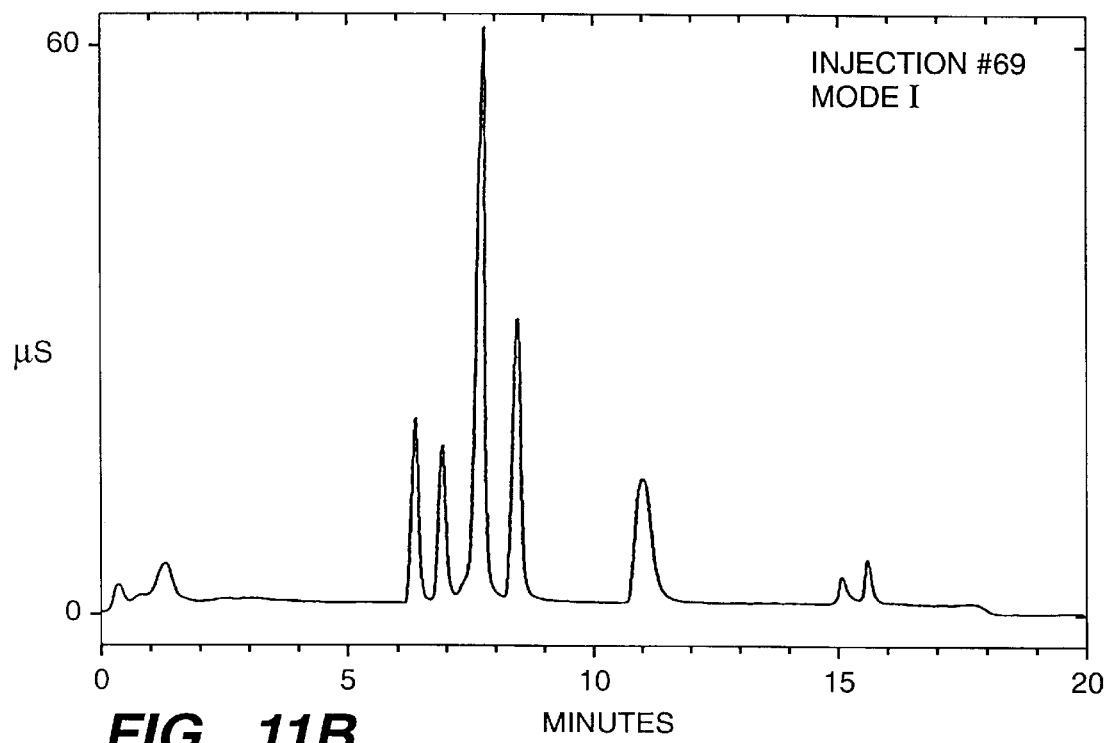
FIG._11B

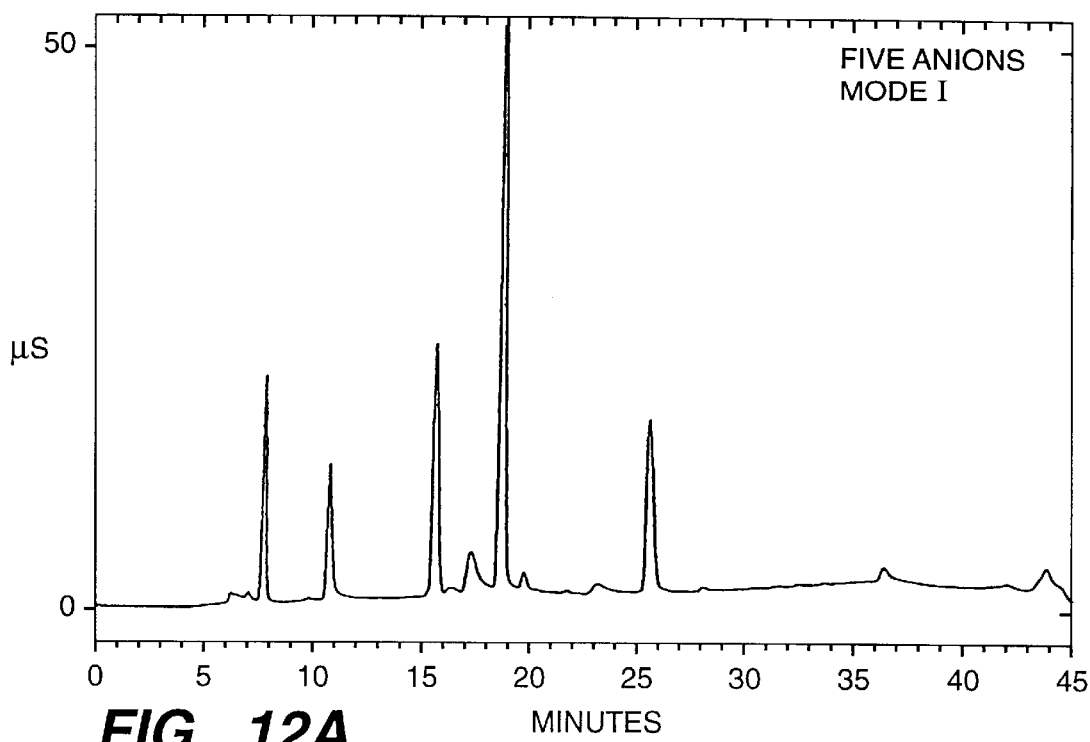
FIG._12A
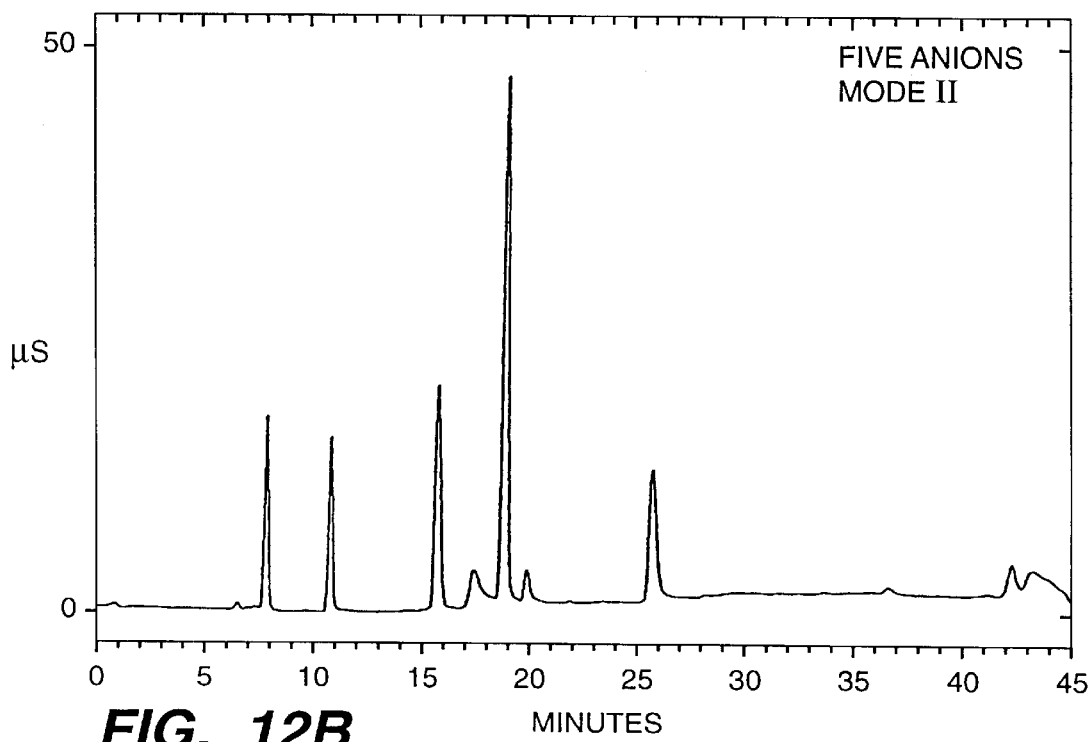
FIG._12B

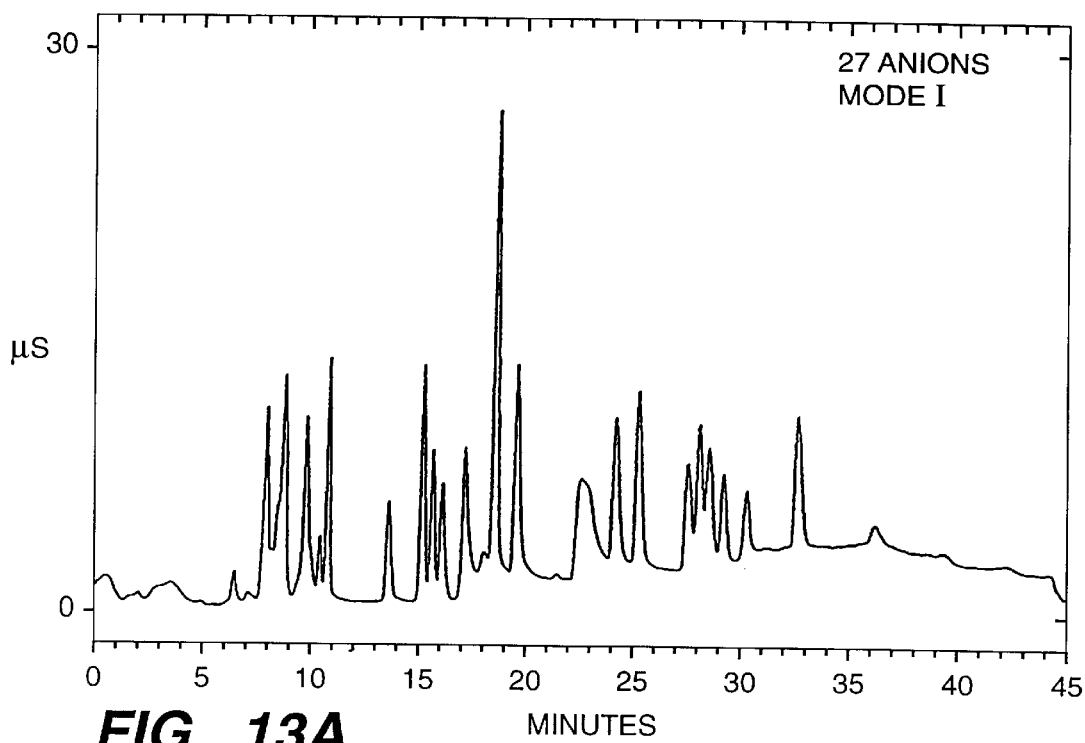
FIG._13A
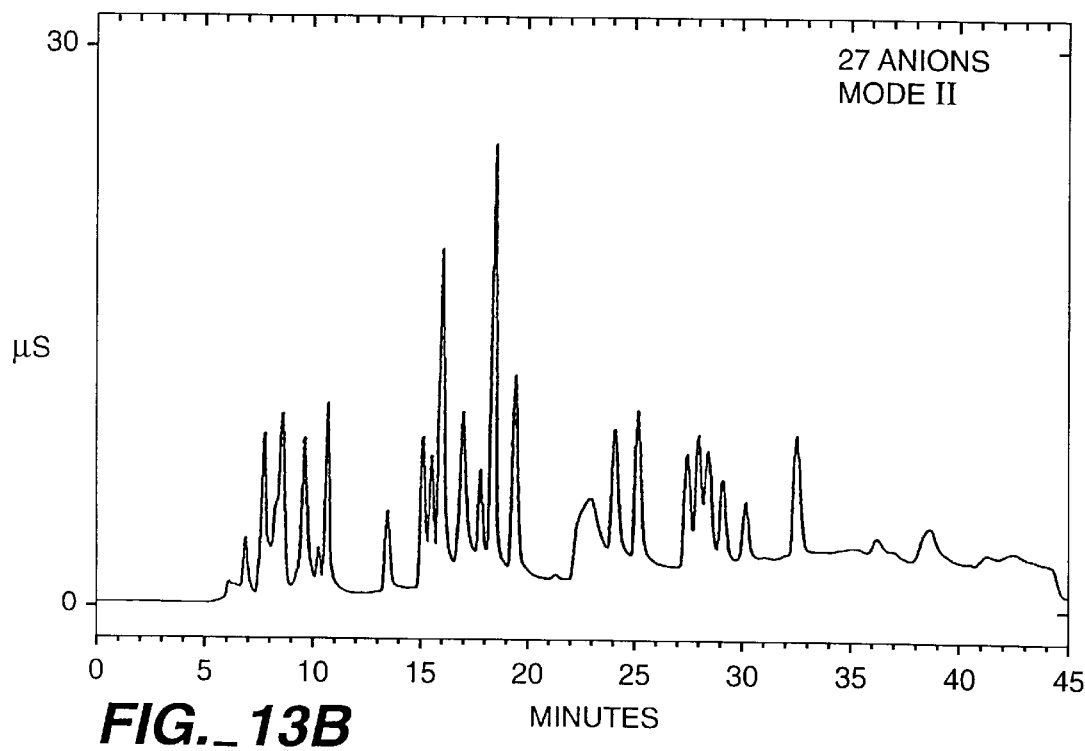
FIG._13B

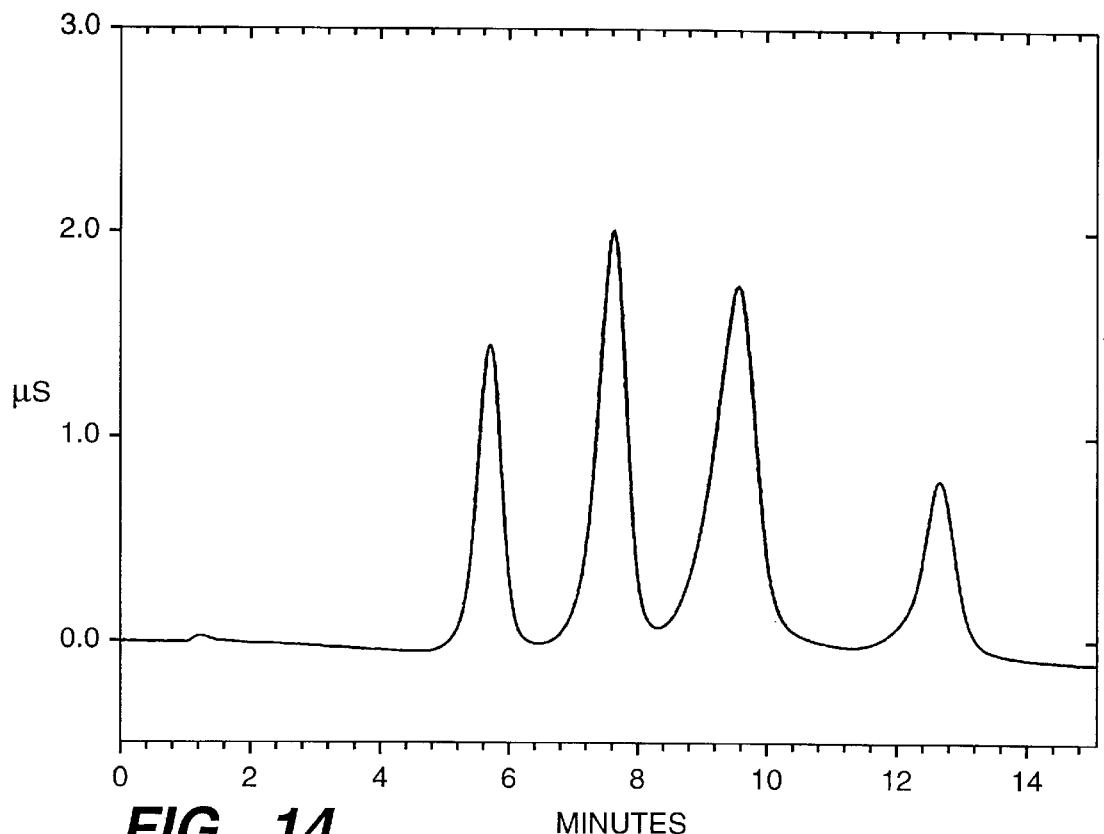
FIG._14
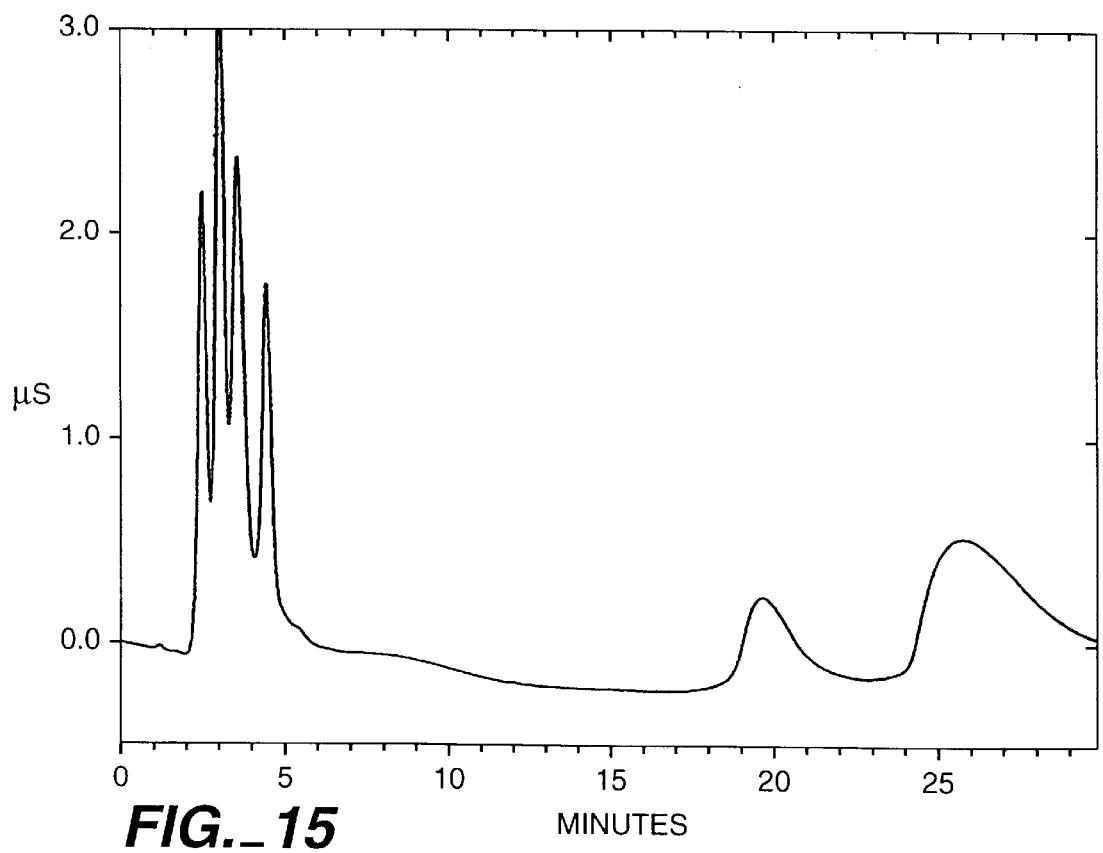
FIG._15

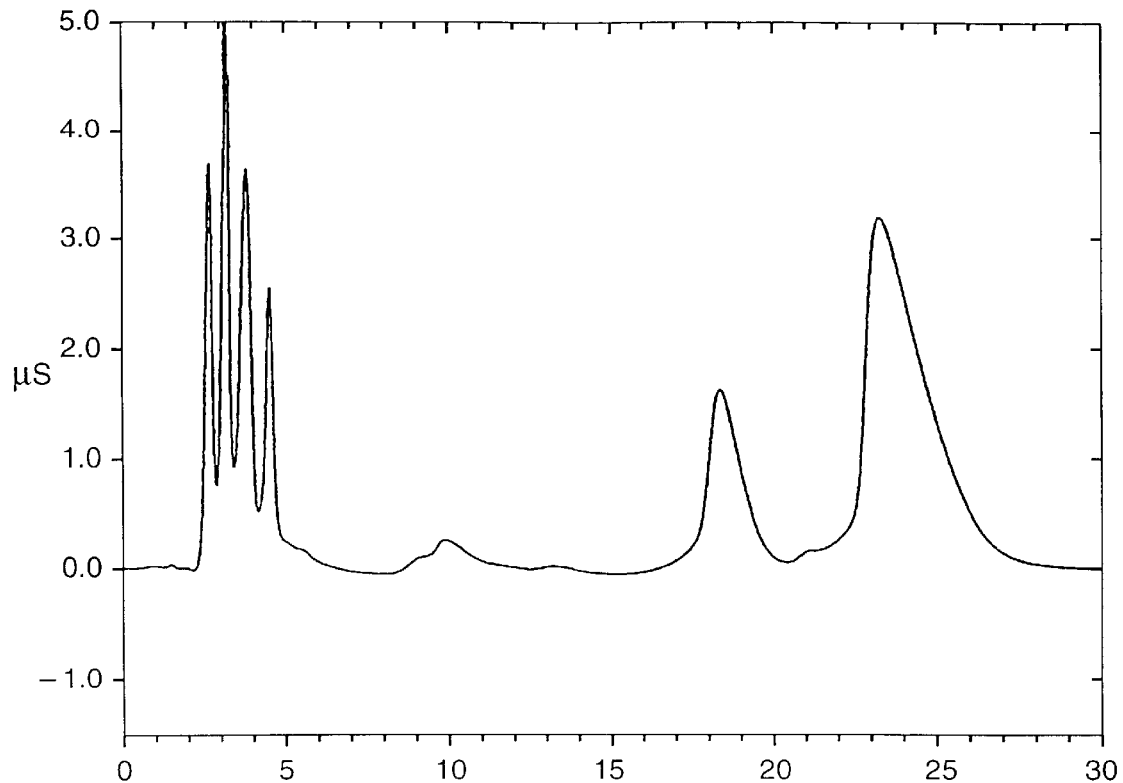
FIG._16
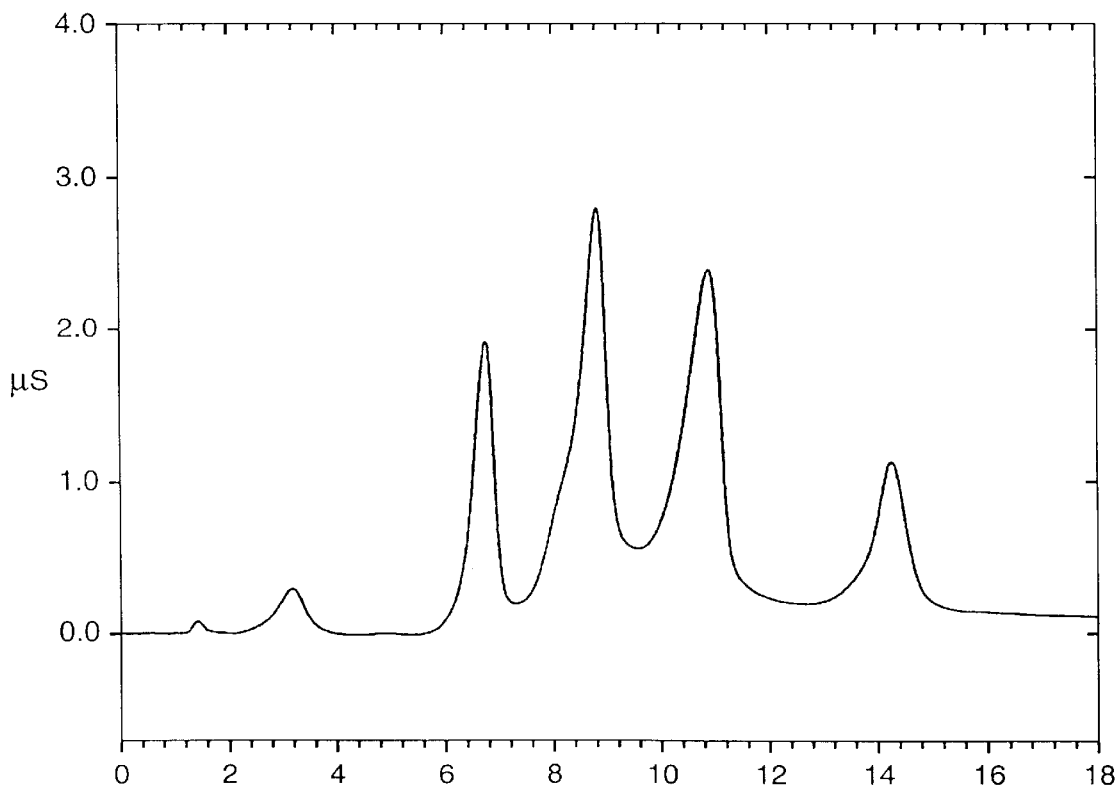
FIG._17

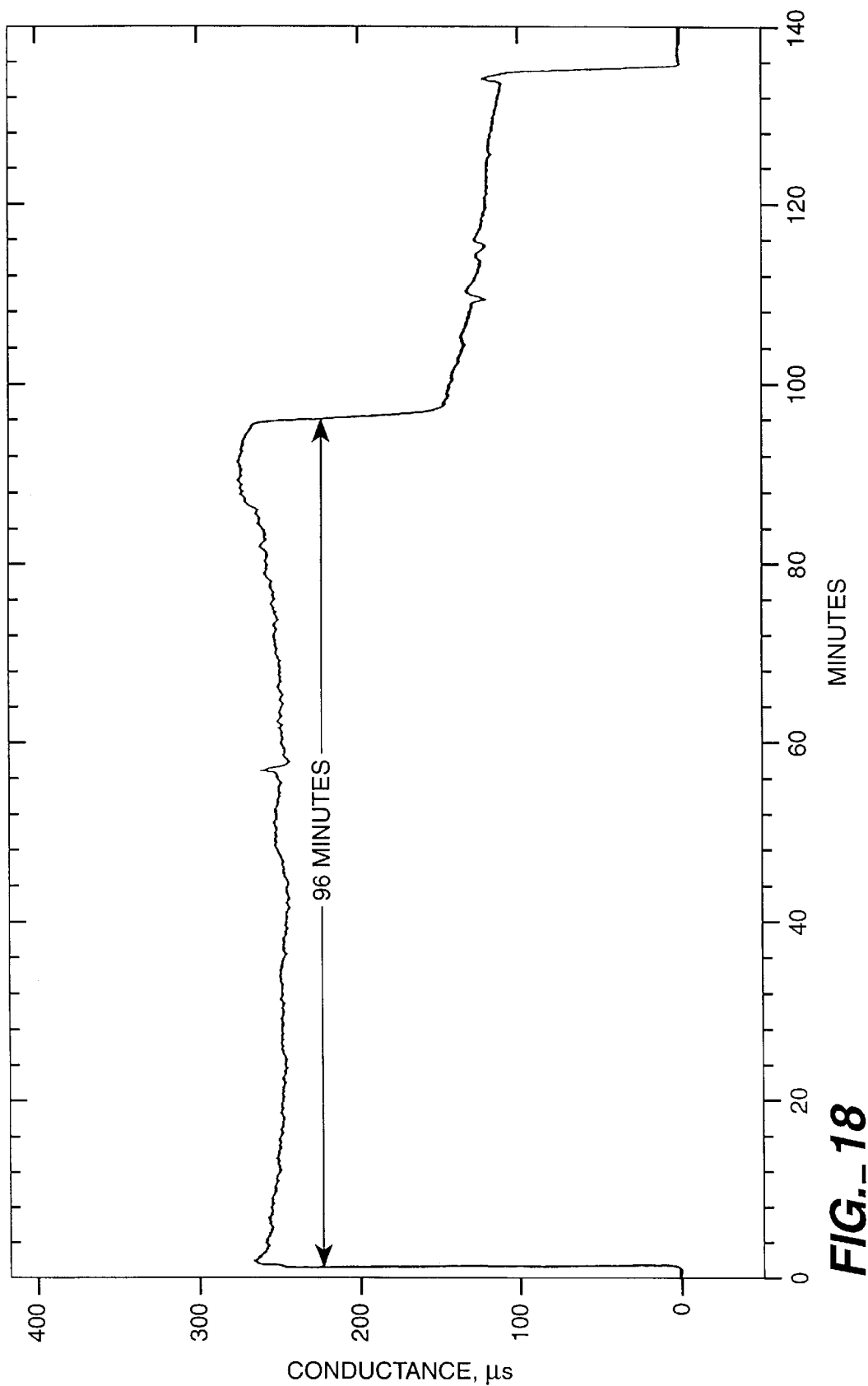
FIG._18

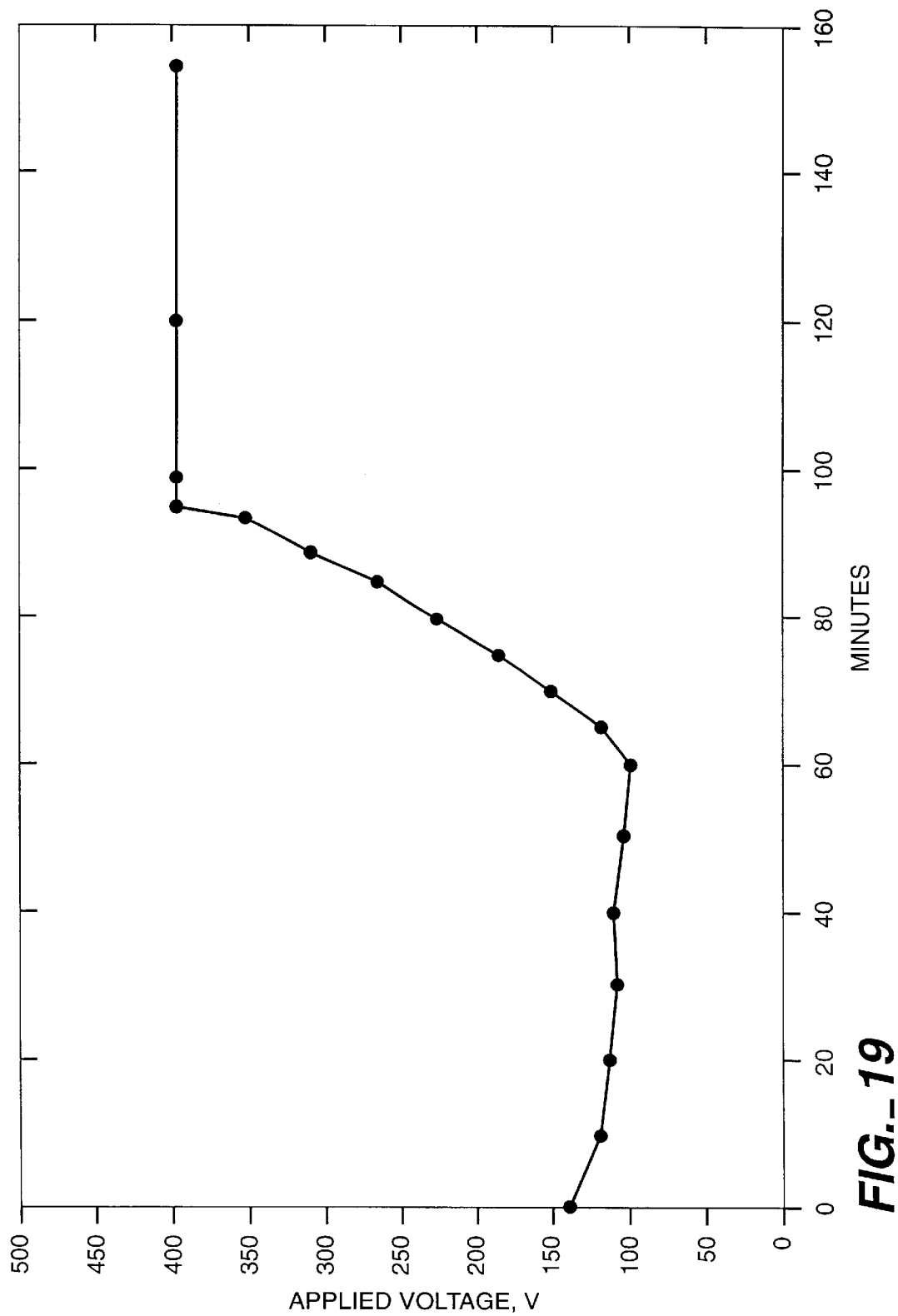
FIG._19

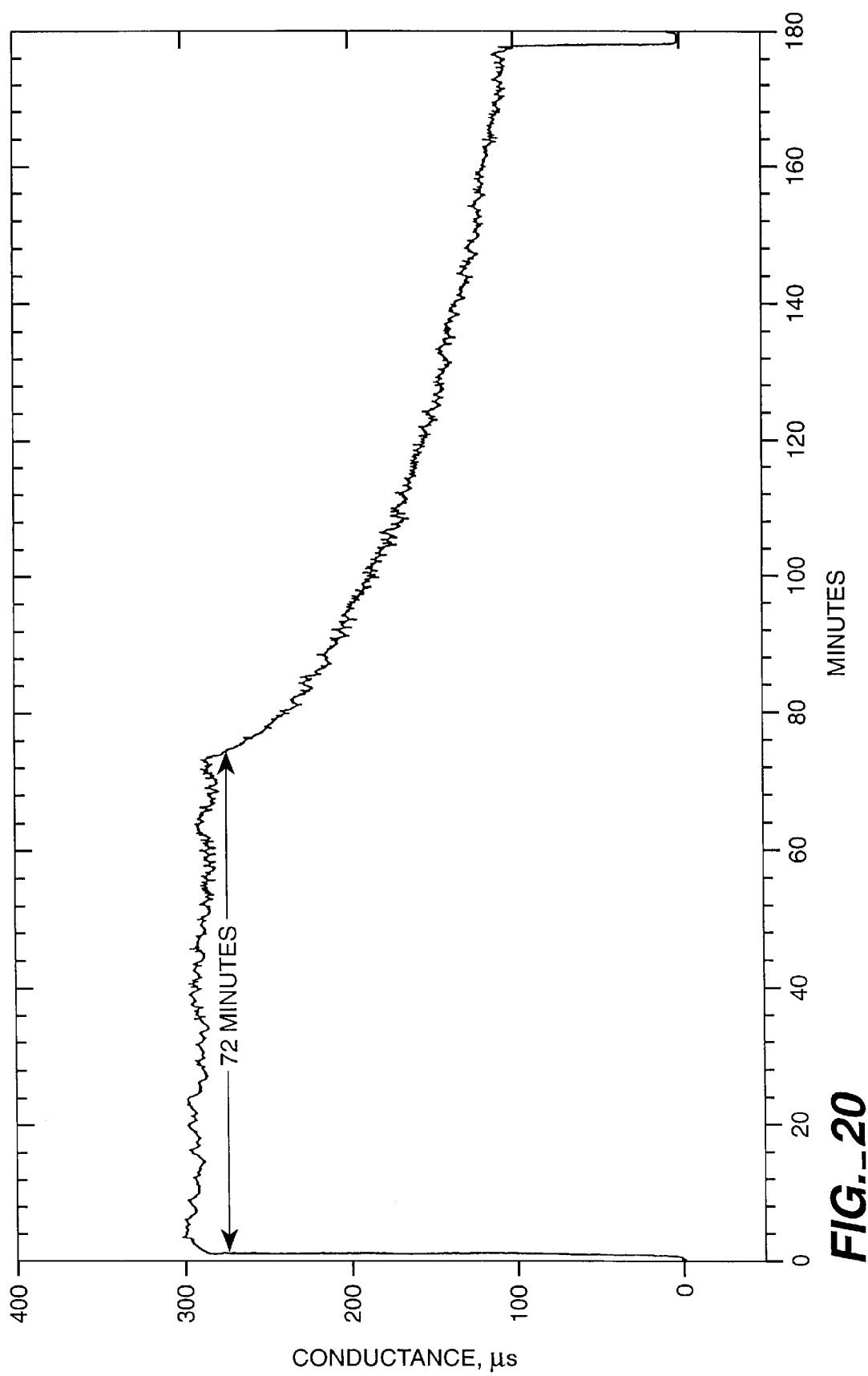
FIG._20

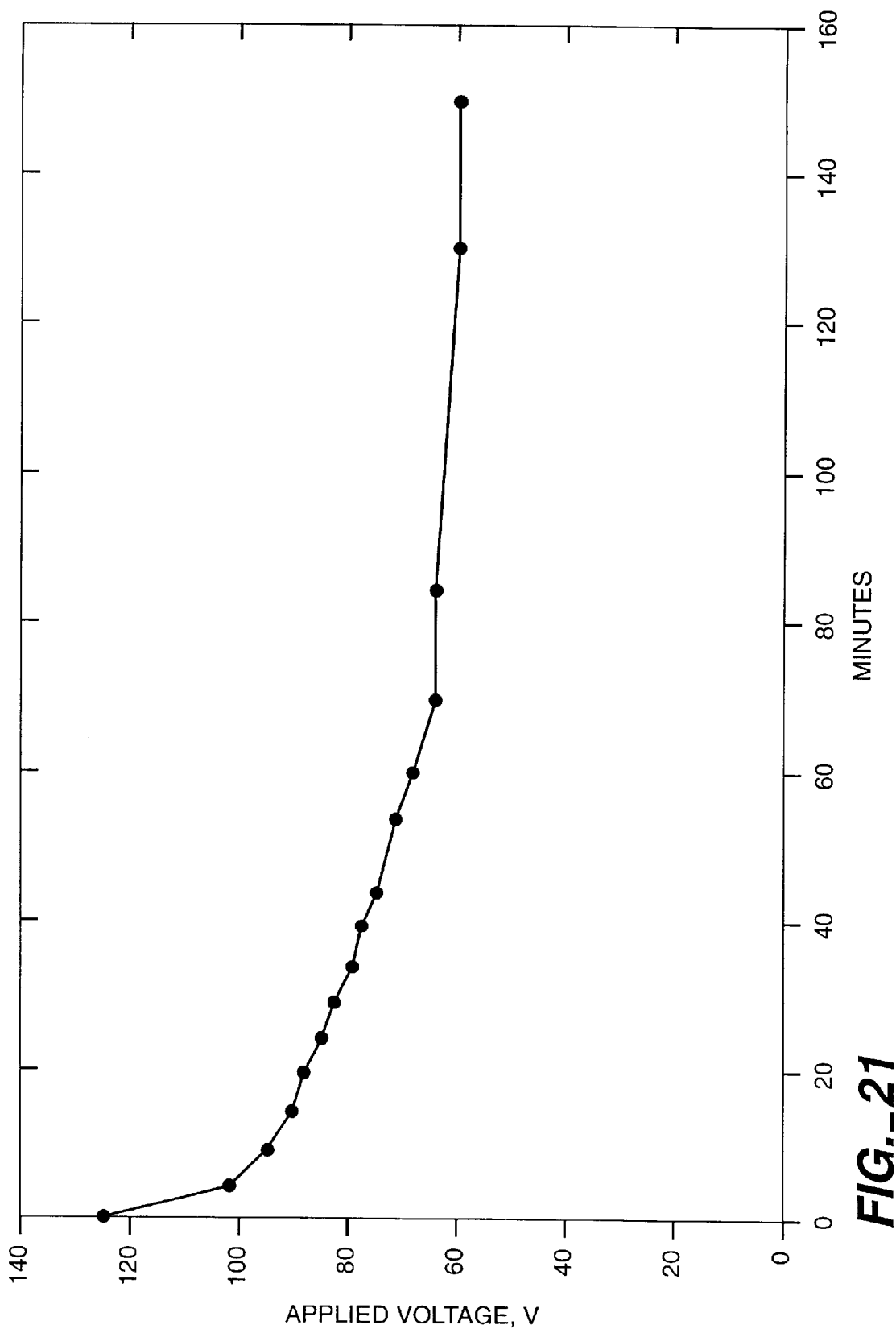
FIG._21

ACID BASE OR GENERATOR

CROSS-REFERENCE TO RELATED APPLICATION

This is a division of application Ser. No. 09/006,096 filed Jan. 13, 1998 now U.S. Pat. No. 6,036,921. Application Ser. No. 09/006,096 is a continuation-in-part of H. Small U.S. patent application Ser. No. 08/783,317, filed Jan. 15, 1997 now abandoned.

BACKGROUND OF THE INVENTION

The present invention relates to a method and apparatus for generation of a high purity acid or base particularly for use as a chromatography eluent.

In liquid chromatography, a sample containing a number of components to be separated is directed through a chromatography separator, typically an ion exchange resin bed. The components are separated on elution from the bed in a solution of eluent. One effective form of liquid chromatography is referred to as ion chromatography. In this known technique, ions to be detected in a sample solution are directed through the separator using an eluent containing an acid or base and thereafter to a suppressor, followed by detection, typically by an electrical conductivity detector. In the suppressor, the electrical conductivity of the electrolyte is suppressed but not that of the separated ions so the latter may be detected by the conductivity detector. This technique is described in detail in U.S. Pat. Nos. 3,897,213, 3,920,397, 3,925,019 and 3,956,559.

There is a general need for a convenient source of high purity acid or base for use, such as an eluent for liquid chromatography and, particularly, for ion chromatography. In one technique, described in U.S. Pat. No. 5,045,204, an impure acid or base is purified in an eluent generator while flowing through a source channel along a permselective ion exchange membrane which separates the source channel from a product channel. The membrane allows selective passage of cations or anions. An electrical potential is applied between the source channel and the product channel so that the anions or cations of the acid or base pass from the former to the latter to generate therein a base or acid with electrolytically generated hydroxide ions or hydronium ions, respectively. This system requires an aqueous stream of acid or base as a starting source or reservoir.

There is a particular need for a pure source of acid or base which can be generated at selected concentrations solely from an ion exchange bed without the necessity of an independent reservoir of an acid or base starting aqueous stream. There is a further need for such a system which can be continuously regenerated. Such need exists in chromatography, and specifically ion chromatography, as well as other analytical applications using acid or base such as in titration, flow injection analysis and the like.

SUMMARY OF THE INVENTION

In accordance with the present invention, a method and apparatus has been provided for generating acid or base in an aqueous stream, such as water alone or in combination with additives (e.g. ones which react with the acid or base or with the sample). The system provides an excellent source of high purity acid or base for use as an eluent for chromatography and, particularly, ion chromatography.

Referring first to a system in which a base is generated for anion chromatographic analysis, an aqueous stream is directed through a flowthrough cation exchange bed including exchangeable cations. An electrical potential is applied between an anode and a cathode in electrical communication with an inlet and an outlet portion of the bed, preferably near the inlet and outlet, respectively, of the bed. Cations on the bed electromigrate into the aqueous stream while hydroxide ions are electrolytically generated to form a base-containing eluent. A liquid sample stream containing anions to be detected together with the generated eluent flow through a chromatographic separator in which the anions are separated. The chromatographic effluent flows past a detector in which separated anions are detected. In one embodiment, between separation and detection, the separated anion stream flows through a flowthrough second cation exchange bed including exchangeable cations and hydronium ions with no electrical potential being applied. The second bed serves as a suppressor with hydronium ions in the bed being displaced by ion exchange with the cations of the base to convert the base to weakly ionized form for conductivity detection.

In a preferred embodiment, after completion of the desired number of cycles, flow through the first and second cation exchange beds is reversed by appropriate valving for the next sample stream. An electrical potential of the type described with respect to the first bed is applied to the second bed while the potential is discontinued in the first bed. Thus, the second bed generates eluent and the first bed suppresses conductivity of the base.

In another embodiment, the second cation exchange bed is disposed after the detector. In this instance, the second bed serves no suppression function. Instead, it serves as a sink or trap to retain the cations of the base and the eluent. By appropriate valving, flow may be reversed through the first and second beds with potential applied in the second bed but not the first bed. During the reversal setting of the valving, the second bed generates the base.

Since hydrogen and oxygen gases are generated in the ion exchange beds which could interfere with detection, it is preferable to pressurize the chromatographic effluent prior to detection, such as by use of a flow restrictor.

BRIEF DESCRIPTION OF THE DRAWINGS

FIG. 1 is a schematic flow diagram of an ion chromatography system using an eluent generator according to the invention, without recycle.

FIG. 2 is an expanded view of an eluent generator according to the invention.

FIGS. 3 and 4 are schematic flow diagrams of an ion chromatography system using eluent generation according to the invention, with recycle, illustrating flow using two different valve settings.

FIGS. 5 and 6 are schematic flow diagrams of a liquid chromatography system using eluent generation according to the invention, with recycle, illustrating flow using two different valve settings.

FIG. 7 is a chart of conductance of KOH vs. current.

FIGS. 8–17 are chromatograms of various experiments performed in accordance with the present invention.

FIGS. 18–21 are comparative exhaustion profiles and operating voltage for single-bed and dual-bed KOH generators.

DETAILED DESCRIPTION OF PREFERRED EMBODIMENTS

The method and apparatus for generation of acid or base according to the present invention will first be described to supply eluent for ion chromatography. For simplicity, although applicable to anion or cation analysis, the system will be described for the analysis of anions on an ion exchange resin packed bed form of an exchange bed. In this instance, the first cation exchange bed generates a base such as an alkali metal hydroxide, typically sodium or potassium. Conversely for analysis of cations, the eluent generated is an acid such as hydrochloric acid.

The system is applicable to the generation of eluent for liquid chromatography forms other than ion chromatography. For example, it is applicable to liquid chromatography using an ultraviolet (UV) detector. The eluent may be in a form (e.g. salt) other than a pure acid or base. Thus, the term "aqueous stream" includes pure water or water with such additives. Also, the terms "eluent comprising a base", "eluent comprising an acid", an "acid" or a "base" mean an aqueous stream including acid or base generated according to the invention regardless of the form it takes on mixing with other reagents present in the aqueous stream.

Referring specifically to FIG. 1, a simplified ion chromatography apparatus is illustrated. The system includes a source of an aqueous stream such as deionized water reservoir 10 which is pumped by chromatography pump 12 to column 14, serving to generate acid or base, through sample injection valve 16 into chromatographic separator 18 packed with a chromatographic separation medium, typically an ion exchange resin packed bed. Alternative other forms of separation medium may be used such as a porous hydrophobic chromatographic resin with essentially no permanently attached ion exchange sites such as described in EPA publication 180,321, incorporated herein by reference.

A column 20 is in fluid communication with separator 18, serving to suppress the conductivity of the base in the effluent from separator 18, but not the conductivity of the ions injected through sample injection port 16.

The effluent from suppressor 20 is directed through a flow-through conductivity cell 22 for detecting the resolved ions in the effluent from suppressor 20. A suitable data system, not shown, is provided in the form of a conventional conductivity detector for measuring the suppressor effluent in the conductivity cell 22. In conductivity cell 22, the presence of an ionic species produces an electrical signal proportional to its concentration. Such signal is typically directed from cell 22 to a conductivity meter (not shown) forming part of a data system permitting direct detection of the concentration of the separated ionic species. With the exception of column 14, such ion chromatography systems are well known, e.g. as illustrated in U.S. Pat. Nos. 3,897,231; 3,920,397; 3,925,019 and 3,956,559 incorporated herein by reference.

The system also includes means for pressurizing the effluent prior to detection to minimize adverse effects of gases (hydrogen and oxygen) generated in the eluent generator 14 as will be described hereinafter. As illustrated in FIG. 1, such pressurizing means comprise a flow restrictor 24 downstream of conductivity cell 22 to maintain the ion chromatography system under pressure.

FIG. 2 illustrates in more detail column 14 of the present invention as a base or acid generator. Column 14, typically in the form of a hollow cylinder 26, contains ion exchange bed 28. Column 14 is shown schematically, and so cylinder 26 is not illustrated with its top and bottom walls or with the inlet and outlet liquid couplings which can be of a conventional type used for packed bed suppressor columns or chromatography separator columns sold by Dionex Corporation. For the generation of base, the bed is of a strongly acidic cation exchange type, preferably a packed ion exchange resin bed. Column 14 also includes electrodes 30 and 32 in the upstream and downstream portions of the cation exchange bed. "Inlet portion" means the inlet side half of the bed and "outlet portion" means the outlet side half of the bed. Alternatively, one or both electrodes may be physically separated from the cation exchange bed so long as the electrodes are in electrical communication with the adjacent bed. For example, an electrically conductive screen may separate one or both of the electrode from the bed.

As illustrated, power supply 33 is connected so that electrode 30 has anode polarity and electrode 32 a cathode polarity. Preferably, the power supply 33 includes a variable outlet potential for reasons which will be described.

The illustrated electrodes 30 and 32 are suitably in the form of porous inert metal disks or frits (e.g. formed of platinum), preferably disposed near the inlet and outlet respectively of the column, serving also as supports holding the resin particles of the packed bed in close contact. By "near the inlet and outlet" is meant placing the electrodes within about 10 to 20% of the inlet and outlet of the bed, respectively, and preferably at the inlet and outlet. The electrodes may be in direct contact with such portions of the bed or may be adjacent to such portions of the bed in electrical contact therewith. Also, the electrodes may take forms other than porous disks (e.g. rings, screens or probes) so long as they provide good contact with the ion exchange bed, preferably by direct contact.

As used herein, the terms "anion exchange bed, cation exchange bed or ion exchange bed" refer to a flow-through bed of ion exchange material through which the aqueous stream flows. The term "cation" excludes hydronium ion and the term "anion" excludes hydroxide ion. Because of its ready availability and known characteristics, a preferred form of ion exchange bed is a packed ion exchange resin bed. It is important that the resin particles be packed in the bed tightly enough to form a continuous ion bridge or pathway for the flow of anions or cations between the electrodes. Also, there must be sufficient spacing for the aqueous stream to flow through the bed without undue pressure drops. For this purpose, the ion exchange resin packing of Dionex Corporation packed bed suppressor columns (Dionex ASC cation exchange resin and Dionex CSC anion exchange resin) may be used.

In the present system, the source or reservoir of cations for generating the base is a cation exchange bed alone or combined with a second cation exchange bed as described below. This is to be contrasted with the eluent generator of U.S. Pat. 5,045,204 in which the reservoir of the acid or base is a preexisting aqueous stream of acid or base which provides the cations or anions which pass transversely through the membrane into the eluent product flow stream. In the present invention, the source of cations or anions is the ion exchange bed and the acid or base is generated during the flow of the aqueous stream through the bed. The present cation exchange bed extends in a network transverse to the flowing aqueous stream and provides an electrical path for cations in contact with both the anode and the cathode. Thus, the definition of ion exchange bed excludes a membrane suppressor structure.

In one form of the invention the entire bed comprises ion exchange material commonly classified as strongly acidic cation type or strongly basic anion type. This embodiment will be referred to as the "single-bed generator". The desired capacity for the single-bed ion exchange material is that which provides a sufficient capacity of generating acid or base for the desired analysis system. It is preferred to use ion exchange materials that have ion exchange capacity ranging from about 0.4 to about 2.4 meq/mL. However, ion exchange materials with either higher or lower capacity may also be used. Examples of suitable cation exchange resins include Dowex 50W, 200–400 mesh resins and Dionex ASC cation exchange resin. The examples of suitable anion exchange resins include Dowex 1, 200–400 mesh resin and Dionex CSC anion exchange resins.

In another form of the invention, the ion exchange bed includes an upstream bed portion and an adjacent downstream bed portion. The ion exchange capacity of the upstream portion is substantially higher than the ion exchange capacity of the downstream bed portion. The upstream bed portion normally contains substantially more (e.g. 10 times or more) ion exchange material than the downstream portion. Usually the upstream portion is of the same cross-sectional area but substantially longer than the downstream bed portion, depending on the system. Thus, the upstream bed portion may be about 10 to 20 longer than the downstream bed portion in a typical system.

The above system will be termed the "dual-bed generator". In the dual-bed base generator, the upstream bed portion preferably comprises a strongly acidic cation exchange resin (e.g., a sulfonated resin in $K^+$ form) and the downstream bed portion preferably comprises a weakly acidic cation exchange form (e.g., a carboxylated resin also in $K^+$ form). Similarly, for the generation of acid, the upstream bed portion is of the strongly basic anion exchange type (e.g., a resin with quaternary amine functional groups) and the downstream bed portion is of the weakly basic anion exchange type (e.g. a resin with tertiary or secondary amine functional groups). For either type of downstream bed portion the capacity preferably is in the range of from about 0.4 to about 2.4 meq/mL. However, ion exchange materials with either higher or lower capacity may also be used. For the downstream bed portion, suitable cation exchange resins include Dionex CS12A resin and Bio-Rex 70 resin, and examples of anion exchange resins include AG 3-X4.

The advantage of using the dual-bed approach can be seen by viewing what may happen in a single-bed base generator, all of the strongly acidic cation exchange resin types. For example, in a KOH generator column of this type, $H^+$ ions generated at the anode displace $K^+$ ions in the bed, and the displaced $K^+$ ions combine with $OH^-$ ions generated at the cathode to produce KOH in the carrier solution (i.e. deionized water) before leaving the generator column. $H^+$ ions migrate faster through the resin bed than $K^+$ ions under the applied field. Once the zone of $H^+$ ions reaches the cathode, some of the applied current is not utilized for generation of KOH, and the concentration of KOH generated becomes lower than what is prescribed by the applied current and carrier flow rate (i.e., the quantitative linear relationship between the KOH concentration and the applied current becomes invalid). Therefore, the useful capacity of a single-bed KOH generator column (defined as the amount of $K^+$ ions producing a constant concentration of KOH when the applied current and the carrier flow rate are constant) is about 40 percent of the total $K^+$ capacity of the generator column.

The dual-bed KOH generator column is an approach to increase the useful capacity of a KOH generator column. In the dual-bed KOH generator column, once $H^+$ ions reach the bed of the weakly acidic resin, their migration through the resin bed is significantly slowed down because of their higher affinity to the weakly acidic functional groups. On the other hand, the migration of $K^+$ ions through the resin bed is little affected. Therefore, more $K^+$ ions are able to reach the cathode to form KOH before the arrival of $H^+$ ions at the cathode, and thus the useful capacity of the KOLI generator column is increased. In the dual-bed KOH generator column, once $H^+$ ions reach the weakly acidic resin bed, the applied voltage needed to maintain the constant current will increase due to the development of the less conductive protonated zone in the weakly acidic resin bed.

The exchangeable cations or anions must also be sufficiently water soluble in base or acid form for use at the desired concentrations. Suitable exchangeable cations are metals, preferably alkali metals such as sodium, potassium, lithium and cesium. Potassium is particularly effective because it is a common, relatively inexpensive species and, of the two common cations, sodium and potassium, a cation exchange resin in potassium form has the lower electrical resistance. Other suitable cations are quaternary ammonium cations such as tetramethyl ammonium, tetraethyl ammonium and tetrabutyl ammonium. For cation analysis, suitable exchangeable anions include chloride, sulfate and methane sulfonate.

For a packed bed, the higher the cross-linking of a resin the higher its capacity (expressed as milliequivalents per ml. of column); therefore, higher cross-linked resins give more compact generators and suppressors. This is desirable. However, the higher the cross-linking of a resin, the less it deforms when packed in a column. Some deformation is desirable in that it improves the area of contact between resin beads thus lowering the electrical resistance of the packed bed. Lower resistance means that a particular level of current may be attained at a lower applied voltage; this, in turn, leads to less heating of the bed while carrying current, a desirable feature.

Bead deformation is favored by lowering the degree of cross linking. But, resin of very low cross-linking (say 1 to 2%) is so deformable that at certain flow rates the deformation can lead to undesirably high pressure across the bed. In summary, a wide range of cross-linking can be used. Resins of moderate cross-linkage are to be preferred, typically in the range of 4 to 16% divinyl benzene for styrene divinyl benzene polymer beads.

Other forms of ion exchange beds can be used such as a porous continuous structure with sufficient porosity to permit flow of an aqueous stream at a sufficient rate for use as an eluent for chromatography without undue pressure drop and with sufficient ion exchange capacity to form a conductive bridge of cations or anions between the electrodes. One form of structure is a porous matrix or a sponge-like material with a porosity of about 10 to 50% permitting a flow rate of about 0.1 to 3 ml/min without excessive pressure drop. Another suitable form is a roll of ion exchange film (e.g. in a configuration of such a roll on a spindle disposed parallel to liquid flow). Electrodes would be placed at each end of the roll which could be textured to provide an adequate void channel.

For the production of pure base (e.g. potassium hydroxide), high purity (deionized) water is pumped to the bed in an accurate and controllable flow rate by a typical high pressure chromatography pump. To generate base while water is flowing through the bed, a D.C. potential is applied between the inlet and outlet of the bed using the inlet porous inert metal disk as the anode and the outlet porous inert metal disk as the cathode. Water splitting takes place at both electrodes. The anode reaction in the upstream portion of the bed is $$H_2O - 2e^- \rightarrow 2H^+ + 1/2\ O_2 \qquad (1)$$

During this reaction, hydronium ions are produced. The hydronium ions pass into the cation exchange resin by electromigration displacing the exchangeable cations (e.g., K+ ions) ahead of them. This displacement takes place along the length of the bed eventually leading to the production of base (e.g., KOH) in the flowing aqueous stream in the vicinity of the cathode. The arriving cations on the column couple with the hydroxide ions produced in the aqueous stream to produce a base. The hydroxide ions are produced in the following cathodic reaction.

$$2\ H_2O+2e^-\rightarrow 2OH^-+H_2 \qquad (2)$$

According to the invention, the concentration of the generated base is readily controlled by correspondingly controlling (1) the flow rate of the aqueous stream through the bed, (2) the electrical current through the bed, and (3) both current and flow simultaneously.

The electrode reactions produce electrolysis gases, hydrogen and oxygen, which are carried forward into the chromatography system. If these gases are produced in significant volume relative to the liquid flow, their presence can be detrimental to chromatographic operation. This potential problem can be eliminated by application of Boyle's law. The system can be operated over a wide range of pressures, e.g., ambient to about 1500 psi above ambient. An elevated pressure (e.g. 250 to 500 psi) is preferred so that the gases are compressed to a volume that is insignificant compared to the flow of the aqueous liquid stream. The pressure necessary to accomplish this depends on the volume of gases produced. One mode of elevating the pressure is to connect a flow restrictor 24 such as a fine bore coiled tubing downstream of the detector (e.g. three meters of 0.005 in. ID). This elevates the pressure throughout the chromatography system upstream of the detector. This pressure is higher than that used for conventional ion chromatography systems. In the present system, it is preferable to construct the conductivity cell to be capable of withstanding a pressure of 1500 psi or more above ambient pressure. A lower pressure of 250 to 500 psi could be used in most conditions. Such system pressure may be high enough to interfere with effective use of membrane suppressors. Accordingly, for this reason and others to be described hereinafter, a packed bed suppressor is preferable.

By using a constant flow of water while with constant current, the device of FIG. 2 generates a constant concentration of base. The relationship of current, water flow rate, and base concentration may be illustrated by the following discussion.

Assume that the current through the bed is a constant 10 milliamps. The rate of charge (ion) transfer to the cathode is therefore 10 millicoulombs per second or 600 millicoulombs per minute. From Faradays Law, it is known that 96,500 coulombs of charge produce one equivalent of ions. Therefore, rounding 96,500 to 100,000, it is calculated that 600 millicoulombs per minute produce 6 microequivalents per minute of base (potassium hydroxide) at the cathode. Consequently, if the flow rate of water is a constant 1 ml/min, the concentration of potassium hydroxide leaving the cathode will be 0.006 M. Higher flow rates of water will yield proportionately lower concentrations of potassium hydroxide while higher currents will yield proportionately higher concentrations.

One of the advantages of the present system is the ability to controllably produce very low concentrations of base required for a particular application. Control may be accomplished solely by adjusting the current.

The aqueous stream in source 10 may be high purity deionized water. However, for some forms of chromatography, and particularly ion chromatography, it may be desirable to modify the source with an additive which reacts with the base generated at the cathode to produce eluents of varying potency. For the production of a base, such well known additives include a source of carbonic or boric acid, phenol, cyanophenol, and the like. For the production of acid, such additives include m-phenylene diamine, pyridine and lysine. The aqueous stream is pumped at rates determined by the analytical process to be used. For ion chromatography, typical flow rates of 0.1 to 3 mL/min are employed.

The current (voltage) requirements of a generator depend on (a) the eluent strength required; (b) the diameter of the column; (c) the length of the column; (d) the electrical resistance of the resin; and (e) the flow rate of the aqueous phase. For example, a fresh 4×150 mm column of potassium form of Dowex 50W×8 run at 8 milliamps and a flow rate of 1 mL/min generates approximately 0.005M potassium hydroxide. The voltage required initially when the bed is fresh is about 160 volts.

As the generator exhausts, that is, as it converts to the hydronium form, its resistance drops and a progressively lower voltage will be required to maintain the current at 8 milliamps.

A sodium form resin which has a higher resistance than the potassium form will require a somewhat higher voltage to produce a certain current all other factors being the same.

To produce a certain current, the voltage applied to a generator will be proportional to its length and inversely proportional to its cross sectional area, all other factors being the same.

It is normally important to maintain a constant current it is directly related to the concentration of acid or base. A feedback loop may be provided to assure sufficient voltage to deliver the predetermined, constant current (e.g. 10 milliamps). Thus, the current is monitored and when the resistance changes, the potential is correspondingly changed by the feedback loop. Therefore, the voltage is a slave to the reading of the current. Thus, it is preferable to supply a variable output potential system of this type (e.g. one sold under the designation Electrophoresis Power Supply EPS 600 by Pharmacia Biotech.

In the simplified system illustrated in FIG. 1, no form of recycle or other regeneration is illustrated. The recycle system described below will serve to recycle the cations on column 14 for continuous use. In one form of application, if column 14 has sufficient capacity, it could be discarded after long term use and replaced when so many exchangeable cations are used that a constant concentration of base is no longer generated under a constant current and a carrier flow rate. Alternatively, the generator could be regenerated by passage of acid or base respectively through column 14 which is off line. However, a preferred form regeneration is by recycle as described below.

The above flow system of FIG. 1 has been described with respect to an ion chromatography system. However, generation by column 14 is broadly applicable to a variety of other analytical systems. For example, it could be used for a liquid chromatography system using a detector other than an ion conductivity detector in which suppressor 20 is not used. An example of detector suitable for such a liquid chromatography system is a UV detector.

The ion chromatography system of the present invention has been described with respect to the generation of base. It is also applicable to the generation of an acid with the appropriate modification of the ion exchange beds and polarity of the electrodes. In this instance, an anion exchange bed is used in column 14 to generate acid. Analogous to the generation of base, the anode is disposed in the downstream upstream portion of the bed, preferably at the outlet, while the cathode is disposed in the upstream portion, preferably at the inlet. The reactions at the anode and cathode are as illustrated in equations (1) and (2) above, respectively. Here, the exchangeable anion (e.g. chloride) is displaced at the entrance of the bed by the hydroxide ions generated at the.cathode. Such anions move along the bed toward the anode where hydronium ions are generated. The anions electromigrate from the bed into the aqueous stream near the anode to form an acid with the hydronium ions.

The foregoing parameters regarding the type of ion exchange bed, potential applied, and the like apply in analogous fashion to the generation of acid as to the generation of base. Suitable anion exchange resins include Dowex 1×8 200–400 mesh and Dionex CSC anion exchange resin. Suitable exchangeable anions used for liquid chromatography may be employed here including chloride, sulfate, methane, sulfonate, phosphate, acetate, phthalate, and benzoate to produce the corresponding acids.

Ion Chromatography Recycle Embodiment

Referring to FIGS. 3 and 4, a preferred embodiment of the system of the present invention for generating base is illustrated in which eluent is continuously regenerated. A system with the valve settings illustrated in FIG. 3 functions the same way as the schematic system of FIG. 1. To simplify the figures, the power supply is only illustrated in the figure in which the potential is applied. Like parts in FIG. 1 will be designated with like numbers in FIGS. 3 and 4.

Referring to FIG. 3, the aqueous stream from source 10 is pumped by pump 12 through valves 40 and 42 into column 14 which generates base as described above. The power supply is connected to apply an electrical potential to anode 30 and cathode 32 at the inlet and outlet, respectively, thereof. A cation exchange bed in column 14 generates base which passes as an eluent through valves 44 and 52, into separator column 18. A sample stream containing anions to be detected is injected through port 16 into separator column 18 in the eluent where the anions are separated. The effluent from column 18 flows through valves 40 and 48, through column 20, through valves 50 and 52 and then through conductivity cell 22 in which the separated anions are detected, through flow restrictor 23, and to waste. In this instance, column 14 generates base while column 20 serves as a conventional suppressor to convert the base to weakly ionized form. During suppression, column 20 which is originally in the hydronium form, is being converted to the cation form. The hydronium form of the column is converted to cation as in a conventional suppressor from the inlet side first. Since no electrical potential is applied to column 20, the power supply is not shown in FIG. 3.

Referring to FIG. 4, the valving is reversed so that the flow of FIG. 3 is discontinued and the flow direction of FIG. 4 commences. As an overview, flow through the injection port, separator column, conductivity cell and restrictor is the same direction. However, flow is reversed through columns 14 and 20. In this instance, column 14 serves as a conventional suppressor with no electrical potential being applied and so the power supply to column 14 is not shown. In FIG. 4, an electrical potential is applied by power supply 60 connected to anode 62 at the inlet portion of column 20 and cathode 64 at the outlet end of column 20.

Flow in the valve setting of FIG. 4 is from aqueous stream source 10 through pump 12, valves 40, 46 and 50, and then through column 20 in an opposite direction to flow through that column in FIG. 3. Column 20 which had been partially converted from the hydronium form to the cation form is used a source of cations to generate base in the same manner as column 14 when it was totally in the cation form at the very beginning of operation illustrated in FIG. 3. Flow from the outlet of column 20 flows through valves 48, 50, and 52, through sample injector port 16 in which the sample is injected, separator column 18 in which the anions from the next sample are separated, valves 40, 42 and 44, and then through column 14 functioning now as a suppressor. From there, the effluent flows through valves 42, 44 and 52 through conductivity cell 22, restrictor 23 and to waste.

While specific valving is illustrated for accomplishing recycle, it is apparent to those of skill in the art that other valving may be employed as long as flow can be reversed between columns 14 and 20.

The parameters and conditions for operating columns 14 and 20 are directly analogous to the operation of columns 20 and 14, respectively, in the valve setting of FIG. 3. Column 20 serves as the eluent generator, while column 14 serves as the suppressor. Thus, it is preferable that the ion exchange beds in columns 20 and 14 have similar characteristics, such as column dimensions and ion exchange capacities, because their functions are reversed in FIG. 4 compared to FIG. 3. Specifically, column 20 becomes a base generator while column 14 becomes a suppressor.

In this system with the valve setting of FIG. 4, cations trapped in the suppressor are used as the source of cations for generating the base. The system provides a source of base for the eluent within the ion exchange bed itself, by reversing the flow and operation of columns 20 and 14 at appropriate intervals. Suitably, this point of reversal is accomplished when approximately 20 to 80% of the eluent generator exchange bed has converted from the cation to the hydronium form or when approximately 20 to 80% of the suppressor has converted from the hydronium form to the cation form. The system is preferably adjusted so that these conversions proceed at substantially the same rates. The system is designed to run a predetermined number of samples (e.g. one) to as many as ten or more, with the valve setting of FIG. 3 before converting to the valve setting of FIG. 4.

On startup, each bed, generator and suppressor can be converted to the half exhausted condition, and thereafter can operate with each bed oscillating about 10% or less on either side of this condition. These conditions permit the analysis of at least one sample between the switching of modes. Preferably, they permit the analysis of a large number of samples between mode switching: for example, samples containing low affinity analytes which would typically require very dilute eluents and place a concomitantly lower demand on the generator and suppressor.

Over a long time, cations from the sample could build up on columns 14 and 20 which may eventually interfere with perpetual regeneration of the eluent generator. This could be addressed by periodically flushing the system with an aqueous acid or base regeneration solution.

Recycle for Liquid Chromatography Systems Other than Ion Chromatography System

The above system of FIGS. 3 and 4 is illustrated with columns 14 and 20 serving dual functions, generating eluent and suppressing the conductivity of the eluent prior to conductivity detection. The system of continuous regeneration also applies to other liquid chromatography systems in which there is no need for, and where it may be undesirable to use a suppressor between the separator column and the detector. In this instance, a column of the same type as columns 14 and 20 could be placed downstream of the detector serving as a trap for the cations or anions which could be recycled using appropriate valving for continuous generation of base or acid. Here, in a second setting of the valving, the flow proceeds in the opposite direction between these two columns with appropriate modifications of the application of the electrical potential. A system of this type is illustrated in FIGS. 5 and 6.

Referring specifically to FIGS. 5 and 6, another preferred embodiment of the system of the present invention for generating base is illustrated in which eluent is continuously regenerated. Here, the system is liquid chromatography using a detector such as a UV-Vis detector. The second column is downstream of the detector because no suppression prior to detection is performed. To simplify the figures, the power supply is only illustrated in the figure in which the potential is applied.

Referring to FIG. 5, the aqueous stream (deionized water) is pumped from source 70, pump 72, valves 74 and 76 into column 78 which generates base as described above. The power supply is connected to apply an electrical potential to anode 80 and cathode 82 at the inlet and outlet, respectively, thereof. A cation exchange bed in column 78 generates base which passes as an eluent through valves 84 and 86, into separator column 88. The sample stream containing a target analyte to be detected is injected through sample injection port 90 and is carried by the eluent into separator column 88 where the target analytes are separated. The effluent from column 88 flows past a suitable detector 92 such as a UV-Vis detector or other non-destructive detector in which the separated analytes are detected. After the detector, the effluent flows through valves 74 and 94 into column 96 which serves as a sink or trap for cations in the base which had been generated in column 78. Column 96 is originally in the hydronium ion form and is converted to the cation form in the same manner as in suppressor 20 described with respect to FIG. 3. However, in this instance, no suppression function is performed because column 96 is downstream from detector 92. Since no electrical potential is applied to column 96 in this valve setting, the power supply is not shown in FIG. 5. The effluent from column 96 flows through valves 98 and 86 through flow restrictor 100 and to waste. Restrictor 100 serves the same function as restrictor 22 in FIGS. 3 and 4.

Referring to FIG. 6, the valving is modified so that the flow of FIG. 5 is discontinued and flow in the direction of FIG. 6 commences. As an overview, flow through the injection port, separator column, detector and restrictor is in the same direction. However, flow is reversed through column 78 and 96. In this valve position, no potential is being applied to column 78 which serves to trap cations in the same manner as column 96 in FIG. 5. Thus, no power supply for column 78 is illustrated. In FIG. 6, an electrical potential is applied by power supply 102 connected to anode 104 and cathode 106 at the inlet and outlet ends, respectively of column 96.

Flow in the valve setting of FIG. 6 is from source 70 through pump 72, valves 74, 94 and 98, and then through column 96 in opposite direction to flow in that column in FIG. 5. Column 96 which had been partially converted from the hydronium ion form to the cation form is used as a source of cations to generate base in the same manner as in column 78 when it was in cation form at the beginning of operation illustrated in FIG. 5. The aqueous stream flows from the outlet of column 96 through valves 94, 98 and 86 through sample injector port 90 in which the sample is injected, and into separator column 88 in which the target analytes are separated. From there, the aqueous stream flows past detector 92 in which the target analytes are detected and then through valves 76 and 84 to column 78 in opposite direction to flow through that column in FIG. 5. Column 78 now serves as a trap or sink for cations in the same manner as column 96 had served as described in FIG. 5. The effluent from column 78 flows through valves 76, 84 and 86 through restrictor 100 and to waste.

While specific valving is illustrated for accomplishing recycle for this liquid chromatography application, it is apparent to those of skill in the art that other valving may be employed so long as flow can be reversed between columns 78 and 96.

The same principles of substantially matching the parameters and conditions for operating columns 78 and 96 apply here as described with respect to the analogous column 20 and 30 with respect to FIGS. 3 and 4.

In order to further illustrate the present invention, the following examples are provided.

EXAMPLE 1

Operation of Single-Bed NaOH Generator

This example illustrates a base (metal hydroxide) generator of the type illustrated in FIG. 2. A column (3-mm ID×175-mm length) was filled with Dowex 50W 200–400 mesh $Na^+$ form and each end fitted with a porous Pt disk. In one experiment, while pumping water through the column at 2 mL/min, the voltage was changed in steps with the current passing through the column. Conductance of the effluent was recorded in Table 1. FIG. 7 shows the excellent linear dependence of conductance on current.

From the conductance one can calculate the concentration of sodium hydroxide produced. One can also calculate the concentration of sodium hydroxide to be expected from the current and water flow rate. In one experiment the current was 1.9 mA and the specific conductance measured for the NagH solution generated was 859 $\mu$s.cm. The conductance corresponded to a concentration of 0.00345 N while one would expect a concentration of 0.0037 N from the current and flow rate. The agreement between these two values is very good.

EXAMPLE 2

Operation of a Single-Bed KOH Generator

In this experiment, water was pumped at 1 ml/min through a bed of potassium form resin carrying a current of 10 mA. The effluent was collected, titrated and found to be 0.0051 N in base. The current through the bed was then reduced to 5 mA and the effluent was determined to be 0.0025 N. This experiment confirmed the linear dependence of effluent concentration on current and illustrates the ability to precisely control the concentration of eluent produced by controlling the current through the column.

EXAMPLE 3

Use of a Single-Bed KOH Generator in Ion Chromatography

The ion chromatographic system, illustrated schematically in FIG. 1, was assembled to test a KOH generator in an IC application. FIG. 8 is the chromatogram obtained for a mixture of fluoride, chloride and nitrate (0.0001 M in each) when the generator was run at 5 mA. FIG. 9 is the chromatogram of the mixture when the generator was run at 10 mA. The elution data are summarized in Table 2.

Ions of lower affinity (fluoride, acetate and formate) were also separated on the same system. The separation of FIG. 10 is remarkable in a number of ways:

1. that the voltage applied to the generator was only 6 V;
2. that the current was only 0.2 mA; and
3. that the concentration of KOH being produced by the generator was only 0.0001 N.

The last feature is noteworthy in that it illustrates how easy it is to prepare potassium hydroxide of such low concentration and preserve it from contamination with carbonate. The challenge of accomplishing this by conventional means, that is by diluting a concentrated solution of KOH while preventing contamination by $CO_2$, underlies the efficacy and convenience of the electrochemical eluent generator.

TABLE 1

| Voltage (volts) | Current (mA) | sp. conductance $\mu s \cdot cm$ |
| --- | --- | --- |
| 0 | 0 | <5 |
| 50 | 1.27 | 87 |
| 100 | 2.7 | 189 |
| 150 | 4.32 | 306 |
| 200 | 6.4 | 444 |
| 300 | 11.9 | 859 |

TABLE 2

| Ion | Current (mA) | $t_E$ (min.) | $t_E - t_{void}$ |
| --- | --- | --- | --- |
| Void | — | 0.90 | 0 |
| fluoride | 10 | 0.95 | 0.05 |
| chloride | 10 | 1.27 | 0.37 |
| nitrate | 10 | 2.22 | 1.32 |
| sulfate | 10 | 4.70 | 3.80 |
| fluoride | 5 | 1.00 | 0.10 |
| chloride | 5 | 1.67 | 0.77 |
| nitrate | 5 | 3.52 | 2.62 |
| sulfate | 5 | 15.7 | 14.8 |

EXAMPLE 4

Eluent Recycle

An experimental system assembled to implement the eluent recycle concept is illustrated in FIGS. 3 and 4. The system consisted of a reservoir of deionized water, pump, KOH generator column, separation column, suppressor column, conductivity cell, and flow restrictor that were interconnected through three Dionex BF-2 double-stack, 4-way, 2-position valves. In a working embodiment, a single-bed KOH generator column (4-mm ID×50-mm length) was packed with a Dionex 18 $\mu$cm cation exchange resin in the $K^+$ form, and a Dionex AS-11 column (4-mm ID×250-mm length) was used as the separation column. The three 4-way valves were automatically switched between their two positions using a computerized controller. A power supply was connected to the KOH generator column using computer-controlled relays.

In the valve position of FIG. 3, column 20 (the KOH generator column) was supplied with current to produce KOH, and Column 30 was used as the suppressor column. The system was operated in this valve position until Column 20 was converted about 50 percent to the $H^+$ form by $H^+$ ions generated at the anode, and Column 30 was converted about 50 percent to the $K^+$ form by $K^+$ ions released from Column 20. At this point, both Columns 20 and 30 had acquired the ability to generate and suppress hydroxide, and the roles of Columns 20 and 30 were reversed by switching the position of the three 4-way, 2-position valves to alter the direction of the eluent flow. The system was then switched between the valve position of FIGS. 3 and 4 for every sample run. In this manner, the KOH eluent was recycled.

In one experiment, the KOH generator column was supplied with a constant current of 18 mA (the applied voltage was 30V) and the eluent flow rate was maintained at 0.5 mL/min (yielding 22 mM KOH). FIG. 11 shows an example of the separation of fluoride, chloride, sulfate, nitrate and phosphate obtained after the system was switched automatically between the positions of FIGS. 3 and 4 for more than 60 sample injections. These results successfully demonstrated that the isocratic ion chromatographic separations of anions can be achieved by implementing the eluent recycle concept.

In another experiment, the current supplied to the KOH generator column was changed from 0.5 mA to 34 mA at a rate of 1.0 mA/min to generate a gradient of KOH from 0.62 mM to 42 mM at a flow rate of 0.5 mL/min. FIG. 12 shows an example of the separation of fluoride, chloride, nitrate, sulfate and phosphate obtained with the system operated in the valve positions of FIGS. 3 and 4.

FIG. 13 shows an example of the separation of a mixture of 27 anions with the system operated in the valve positions of FIGS. 3 and 4. These results successfully demonstrated that the eluent recycle concept can be utilized to achieve gradient ion chromatographic separations of anions.

EXAMPLE 5

Single-Bed Hydrochloric Acid Generator

A 4-mm ID×150-mm long column of the type illustrated in FIG. 2 was filled with Dowex 1×8, 200–400 mesh, in the chloride form. The column was equipped with porous platinum bed supports (electrodes). The chromatography system illustrated schematically in FIG. 1 was assembled to test the HCl generator.

In one test, water was pumped through the system at 1 ml/min, while a voltage (251 V) was applied to the generator giving a current of 2.1 mA. Ten microliters of sample was injected. The sample contained $Li^+$ at 5 mg/mL; Na+, $K^+$, and $Mg^{2+}$ at 20 mg/mL; $NH^+$ at 40 mg/mL; and $Ca^{2+}$ at 100 mg/mL. The run was terminated when the alkali metals and ammonium had eluted and the chromatogram is shown in FIG. 14.

In another test, the generator was polarized at 311 V which generated a current of 8.1 mA and a similar sample injected. In this instance the run was continued until magnesium and calcium had eluted. That chromatogram is illustrated in FIG. 15.

EXAMPLE 6

Single-Bed Methane Sulfonic Acid Generator

A quantity of Dowex 1×8, 200–400 mesh, chloride form was washed with a copious amount of 1.0 N NaOH in order to convert the resin to substantially the hydroxide form. The resin was then neutralized with methane sulfonic acid (MSA) to convert it to the methane sulfonate form.

Using the same procedure as the HCl generator, a 4-mm ID×150-mm length column was filled with the Dowex 1×8 methane sulfonate resin, equipped with porous Pt electrodes and tested.

In one test, the MSA generator was pumped with water a 1 ml/min, polarized (275 V) to give a current of 8.1 mA and the six cation standard sample (see Example 5) injected. The chromatogram is shown in FIG. 16.

In another test, the generator was polarized at 88V giving a current of 1.9 mA and the six cation standard injected. This run was terminated when ammonium and the alkali metals had eluted. The chromatogram is shown in FIG. 17.

EXAMPLE 7

Sponge-like Bed Generator

In this example, a flow-through, sponge-like ion exchange bed is formed. Styrene and divinyl benzene are copolymerized in the presence of an appropriate catalyst and a porogen. A porogen is an added material which, when removed after the polymerization is complete, creates a macroporosity in the polymerized structure. This porosity should be such that it provides for ready flow of liquids through the polymer phase while at the same time providing adequate area of contact between the polymer and the liquid phase. The porogen can be a finely divided solid which can be easily removed by dissolution in acid or base, e.g., calcium carbonate or silica, or it can be a solvent which is rejected by the polymer as it forms and is subsequently displaced by another solvent or water. Examples of suitable liquid porogens include an alcohol such as dodecyl alcohol, e.g. used in the manner described in *Analytical Chemistry*, Vol. 68, No. 2, pp. 315–321, Jan. 15, 1996.

After the porogen is removed, the polymer is sulfonated by commonly known sulfonating agents such as concentrated sulfuric acid or chloro-sulfonic acid. A suitable shape for the polymer is a cylindrical rod which, after sulfonation and conversion to a suitable metal ion form, can be placed in the bore of a chromatography column typically 4 mm in internal diameter. Preferably, the ion exchange rod is introduced into the column in a slightly shrunken form so that in its typical use environment it swells to form a tight fit with the wall of the column. Excess rod is trimmed from the end of the column which is then equipped with porous platinum electrodes and end fittings. Such a column is now ready for use as a base generator in a chromatography application or as a base generator and a suppressor for the determination of anions by ion chromatography.

EXAMPLE 8

Film-type Bed Generator

In this example, a film-type ion exchange bed is formed. A strip of cation exchange membrane in an appropriate metal ion form is rolled on to a solid spindle whose diameter is approximately 5 mm. The width of the film and the length of the spindle are preferably identical. Enough film is added to the spindle to give a final diameter of approximately 15 mm. The film spindle assembly is then placed in a snug fit within a hollow cylinder of the same length as the spindle and this assembly is equipped with porous platinum electrodes and end fittings. The rolling of the membrane film should be loose enough to permit ready flow of aqueous phase parallel to the film while providing adequate exchange of ions between the film and the aqueous phase and minimum band spreading when used as part of a chromatography system. In order to satisfy these requirements of flow, favorable ion exchange rates and chromatographic behavior, an ion exchange membrane with a textured surface may be preferred over a membrane with a very smooth surface; the texturing will act as a separator holding the membrane sufficiently open to allow adequate aqueous flow while providing the other desirable attributes.

Such a device is now ready for use as a base generator in a typical chromatography application or as a base generator and a suppressor for the determination of anions by ion chromatography.

EXAMPLE 9

Comparison of Single-Bed and Dual-Bed KOH Generators

A 4-mm ID dual-bed KOH generator column consisting of a 63-mm length bed of an upstream strongly acidic resin and a 14-mm length bed of a downstream weakly acidic resin was prepared. An 18-$\mu$m sulfonated styrene/divinylbenzene resin in $K^+$ form was used as the strongly acidic resin. A 10-$\mu$m macroporous styrene/divinylbenzene resin with surface-grafted $\alpha$-chloroacrylic acid functional groups in $K^+$ form was used as the weakly acidic resin. The resins were directly adjacent and in contact. The anode was at the inlet of the strongly acidic resin and the cathode at the weakly acid outlet.

As a comparison, a single-bed KOH generator column of the same dimensions (4-mm ID×77-mm length) packed with the 18-$\mu$m sulfonated styrene/divinylbenzene resin was also prepared. The single-bed and dual-bed KOH generator columns were tested using a constant current of 15 mA and a carrier flow rate of 1.0 m/min. The concentration of KOH in the generator column effluent was monitored by measuring the conductance of the effluent with a conductivity detector.

The exhaustion profile and operating voltage obtained for the dual-bed KOH generator column are shown in FIGS. 18 and 19. The dual-bed KOH generator column produced a relatively constant output of KOH (9.3 mM KOH at 1.0 mL/min) for 96 minutes, equivalent to a useful capacity of 0.90 meq KOH (60% utilization capacity). The applied voltage decreased from 145 V at the beginning of the operation to 100 V at 60 min, and then increased to 400 V at 100 min due to the development of the less conductive protonated zone in weakly acidic resin bed. The exhaustion profile and operating voltage obtained for the single-bed KOH generator column are shown in FIGS. 20 and 21. The single-bed KOH generator column produced a relatively constant output of KOH (9.3 mM KOH at 1.0 mL/min) for 72 minutes, equivalent to a useful capacity of 0.67 meq KOH (36% utilization capacity). The applied voltage decreased gradually from 125 V at the beginning of the operation to 60 V at 150 minutes. In comparison, the useful capacity of the dual-bed KOH generator column was 34 percent higher than that of the single-bed KOH generator column. Thus, the dual-bed eluent generator column is a viable approach to increase the useful capacity of the KOH generator column.

What is claimed is:

1. A method of generating an eluent and using the same in anion analysis comprising (a) flowing a first aqueous stream in a first direction through a flowthrough first cation exchange bed including exchangeable cations and having an inlet portion and an outlet portion, while applying an electrical potential between an anode in electrical communication with the inlet portion of said first cation exchange bed and a cathode in electrical communication with the outlet portion of said first cation exchange bed to electrolytically generate hydroxide ions and to electromigrate exchangeable cations into said first aqueous stream to form a first eluent comprising a base, said first cation exchange bed comprising an upstream bed portion comprising a strongly acidic cation exchange material and an adjacent downstream bed portion comprising a weakly acidic cation exchange material, (b) flowing a first liquid sample stream containing anions to be detected and said first eluent through a chromatographic separator in which said anions to be detected are separated, forming a first chromatography effluent, and (c) flowing said first chromatography effluent, with or without further treatment, past a detector in which the separated anions in said first chromatography effluent are detected.

2. The method of claim 1 in which said cathode is in said outlet portion and said base is formed in said first cation exchange bed and flows from there through said chromatographic separator.

3. The method of claim 1 in which said first cation exchange bed comprises a first cation exchange resin packed bed.

4. The method of claim 1 in which said anode and said cathode are in direct contact with said first cation exchange bed.

5. The method of claim 1 further comprising between steps (b) and (c) the step of
   (d) flowing said first chromatography effluent through a flowthrough second cation exchange bed including exchangeable cations and hydronium ions to substitute said exchangeable hydronium ions with the cations of said first eluent base to convert said base to weakly ionized form, said first chromatography effluent exiting as a first suppressed effluent which flows past said detector.

6. The method of claim 5 in which said second cation exchange bed comprises a second cation exchange resin packed bed.

7. The method of claim 5 in which after step (c) the flow of steps (a), (b), (d), (c) is discontinued, said method further comprising
   (e) flowing a second aqueous stream in a second direction opposite to said first direction through said second cation exchange bed, while passing an electric current to electrolytically generate and displace exchangeable cations on said second cation exchange bed into said second aqueous stream to form a second eluent comprising a base which exits said second cation exchange bed,
   (f) flowing a second sample containing anions to be detected and said second eluent through said chromatographic separator in which said anions in said second sample are separated, forming a second chromatography effluent,
   (g) flowing said second chromatographic effluent in said second direction through said first cation exchange bed further including exchangeable hydronium ions to convert said second eluent base to weakly ionized form and replenishing exchangeable cations on said first cation exchange bed depleted during step (a), said second chromatography effluent exiting as a second suppressed effluent, and
   (h) flowing said second suppressed effluent past said detector in which the separated anions in said second suppressor effluent are detected.

8. The method of claim 1 in which in step (a) said aqueous stream is electrolyzed during passage of said electrical current to generate hydrogen and oxygen gases, said method further comprising
   (d) pressurizing the first chromatography effluent prior to detection in step (c) to minimize adverse affects of said gases on detection of said first sample anions.

9. The method of claim 1 in which said exchangeable cations in said first cation exchange resin bed are partially depleted during step (a), said method further comprising discontinuing the flow of said first aqueous stream and flowing a regenerating aqueous stream comprising a base through said first cation exchange bed to at least partially replenish said exchangeable cations.

10. The method of claim 1 further comprising after step (c) the step of
    (d) flowing said first chromatography effluent from said detector through a second cation exchange bed including exchangeable hydronium ions which are substituted by the cations of said first eluent.

11. The method of claim 10 in which after step (d) the flow of steps (a)–(d) is discontinued, said method further comprising
    (e) flowing, an aqueous stream in a second direction opposite to said first direction through said second cation exchange bed including exchangeable cations while passing an electric current to electrolytically generate and displace said exchangeable cations in said second cation exchange bed into said second aqueous stream to form a second eluent comprising a base which exits said second cation exchange bed,
    (f) flowing a second sample containing anions to be detected and said second eluent through said chromatographic separator in which said anions in said second sample are separated, forming a second chromatographic effluent,
    (g) flowing said second chromatography effluent through said detector in which the separated anions in said second chromatography effluent are detected, and
    (h) flowing said second chromatographic effluent in said second direction through said first cation exchange bed including exchangeable hydronium ions which are substituted by the cations of said second eluent, replenishing exchangeable cations lost on said first cation exchange bed depleted during step (a).

12. The method of claim 1 in which said detection in step (c) is by electrical conductivity detection.

13. The method of claim 1 in which said upstream portion has a total ion exchange capacity at least about 10 times that of said downstream bed portion.

14. A method of generating an eluent and using the same in cation analysis comprising
    (a) flowing a first aqueous stream in a first direction through a flowthrough first anion exchange bed including exchangeable anions and having an inlet portion and an outlet portion, while applying an electrical potential between a cathode in electrical communication with the outlet portion of said first anion exchange bed and an anode in electrical communication with the outlet portion of said first anion exchange bed to electrolytically generate hydronium ions and to electromigrate exchangeable anions into said first aqueous stream to form a first eluent comprising an acid, said first anion exchange bed comprising an upstream bed portion comprising a strongly basic anion exchange material and an adjacent downstream bed portion comprising a weakly basic anion exchange material,
    (b) flowing a first liquid sample stream containing cations to be detected and said first eluent through a chromatographic separator in which said cations to be detected are separated, forming a first chromatography effluent, and
    (c) flowing said first chromatography effluent, with or without further treatment, past a detector in which the separated cations in said first chromatography effluent are detected.

15. The method of claim 14 in which said cathode is in said outlet portion and said base is formed in said first cation exchange bed and flows from there through said chromatographic separator.

16. The method of claim 14 in which said first anion exchange bed comprises a first anion exchange resin packed bed.

17. The method of claim 14 in which said anode and said cathode are in direct contact with said first anion exchange bed.

18. The method of claim 14 further comprising between steps (b) and (c) the step of
    (d) flowing said first chromatography effluent through a flowthrough second anion exchange bed including exchangeable anions and hydroxide ions to substitute said exchangeable hydroxide ions with the anions of said first eluent acid to convert said acid to weakly ionized form, said first chromatography effluent exiting as a first suppressed effluent which flows past said detector.

19. The method of claim 18 in which said second anion exchange bed comprises a second anion exchange resin packed bed.

20. The method of claim 14 in which in step (a) said aqueous stream is electrolyzed during passage of said electrical current to generate hydrogen and oxygen gases, said method further comprising (d) pressurizing the first chromatography effluent prior to detection in step (c) to minimize adverse affects of said gases on detection of said first sample anions.

21. The method of claim 18 in which after step (c) the flow of steps (a), (b), (d), (c) is discontinued, said method further comprising (e) flowing a second aqueous stream in a second direction opposite to said first direction through said second anion exchange bed, while passing an electric current to electrolytically generate and displace exchangeable anions on said second anion exchange bed into said second aqueous stream to form a second eluent comprising an acid which exits said second anion exchange bed, (f) flowing a second sample containing cations to be detected and said second eluent through said chromatographic separator in which said cations in said second sample are separated, forming a second chromatography effluent, (g) flowing said second chromatographic effluent in said second direction through said first anion exchange bed further including exchangeable hydroxide ions to convert said second eluent acid to weakly ionized form and replenishing exchangeable anions on said first anion exchange bed depleted during step (a), said second chromatography effluent exiting as a second suppressed effluent, and (h) flowing said second suppressed effluent past said detector in which the separated cations in said second suppressor effluent are detected.

22. The method of claim 14 in which said exchangeable anions in said first anion exchange resin bed are partially depleted during step (a), said method further comprising discontinuing the flow of said first aqueous stream and flowing a regenerating aqueous stream comprising an acid through said first cation exchange bed to at least partially replenish said exchangeable anions.

23. The method of claim 14 further comprising after step (c) the step of (d) flowing said first chromatography effluent from said detector through a second anion exchange bed including exchangeable hydroxide ions which are substituted by the anions of said first eluent.

24. The method of claim 23 in which after step (d) the flow of steps (a)–(d) is discontinued, said method further comprising (e) flowing an aqueous stream in a second direction opposite to said first direction through said second anion exchange bed including exchangeable anions while passing an electric current to electrolytically generate and displace said exchangeable anions in said second anions exchange bed into said second aqueous stream to form a second eluent comprising an acid which exits said second anion exchange bed, (f) flowing a second sample containing cations to be detected and said second eluent through said chromatographic separator in which said cations in said second sample are separated, forming a second chromatographic effluent, (g) flowing said second chromatography effluent through said detector in which the separated cations in said second chromatography effluent are detected, and (h) flowing said second chromatographic effluent in said second direction through said first anion exchange bed including exchangeable hydroxide ions which are substituted by the anions of said second eluent, replenishing exchangeable anions on said first anion exchange bed during step (a).

25. The method of claim 14 in which said detection in step (c) is by electrical conductivity detection.

26. The method of claim 14 in which said upstream portion anion exchange material has a capacity at least about 10 times that of said downstream bed portion anion exchange material.

* * * * *

UNITED STATES PATENT AND TRADEMARK OFFICE
CERTIFICATE OF CORRECTION

PATENT NO. : 6,316,270 B1
DATED : November 13, 2001
INVENTOR(S) : Hamish Small et al.

It is certified that error appears in the above-identified patent and that said Letters Patent is hereby corrected as shown below:

<u>Column 6,</u>
Line 3, change "KOLI" to -- KOH --.

<u>Column 12,</u>
Line 34, change "1.9" to -- 11.9 --.

<u>Column 13,</u>
Line 43, change "μcm" to -- μm --.

Signed and Sealed this

Sixth Day of August, 2002

Attest:

JAMES E. ROGAN
Attesting Officer  Director of the United States Patent and Trademark Office